(12) United States Patent
Takulapalli

(10) Patent No.: US 10,514,380 B2
(45) Date of Patent: Dec. 24, 2019

(54) FIELD EFFECT TRANSISTOR, DEVICE INCLUDING THE TRANSISTOR, AND METHODS OF FORMING AND USING SAME

(71) Applicant: Bharath Takulapalli, Chandler, AZ (US)

(72) Inventor: Bharath Takulapalli, Chandler, AZ (US)

( * ) Notice: Subject to any disclaimer, the term of this patent is extended or adjusted under 35 U.S.C. 154(b) by 0 days.

(21) Appl. No.: 15/156,213

(22) Filed: May 16, 2016

(65) Prior Publication Data

US 2016/0258941 A1    Sep. 8, 2016

Related U.S. Application Data

(63) Continuation of application No. 14/391,661, filed as application No. PCT/US2013/035852 on Apr. 9, 2013, now Pat. No. 9,341,592.

(Continued)

(51) Int. Cl.
| | |
|---|---|
| *G01N 33/543* | (2006.01) |
| *H01L 29/06* | (2006.01) |
| *H01L 29/10* | (2006.01) |
| *H01L 21/301* | (2006.01) |
| *H01L 29/66* | (2006.01) |

(Continued)

(52) U.S. Cl.
CPC ..... *G01N 33/54373* (2013.01); *C12Q 1/6874* (2013.01); *G01N 27/414* (2013.01); *G01N 27/4145* (2013.01); *G01N 27/4146* (2013.01); *G01N 33/48721* (2013.01); *G01N 33/54366* (2013.01); *G01N 33/552* (2013.01); *H01L 21/30604* (2013.01); *H01L 29/0665* (2013.01);

(Continued)

(58) Field of Classification Search
CPC ........... G01N 33/54373; G01N 27/414; G01N 27/4145; G01N 27/4146; B82Y 15/00; C12Q 1/6874

See application file for complete search history.

(56) References Cited

U.S. PATENT DOCUMENTS

| | | | |
|---|---|---|---|
| 5,234,566 | A | 8/1993 | Osman et al. |
| 5,264,395 | A | 11/1993 | Bindal et al. |

(Continued)

FOREIGN PATENT DOCUMENTS

| | | |
|---|---|---|
| CN | 101668866 | 3/2010 |
| CN | 101896814 | 11/2010 |

(Continued)

OTHER PUBLICATIONS

International Search Report and Written Opinion dated May 3, 2009 in Application No. PCT/US2008/066190.

(Continued)

*Primary Examiner* — Matthew L Reames
*Assistant Examiner* — John A Bodnar
(74) *Attorney, Agent, or Firm* — Snell & Wilmer L.L.P.

(57) ABSTRACT

The present disclosure provides an improved field effect transistor and device that can be used to sense and characterize a variety of materials. The field effect transistor and/or device including the transistor may be used for a variety of applications, including genome sequencing, protein sequencing, biomolecular sequencing, and detection of ions, molecules, chemicals, biomolecules, metal atoms, polymers, nanoparticles and the like.

19 Claims, 10 Drawing Sheets

Related U.S. Application Data

(60) Provisional application No. 61/621,966, filed on Apr. 9, 2012, provisional application No. 61/802,235, filed on Mar. 15, 2013.

(51) Int. Cl.
| | | |
|---|---|---|
| *G01N 27/414* | (2006.01) | |
| *G01N 33/487* | (2006.01) | |
| *C12Q 1/68* | (2018.01) | |
| *G01N 33/552* | (2006.01) | |
| *C12Q 1/6874* | (2018.01) | |
| *H01L 21/306* | (2006.01) | |

(52) U.S. Cl.
CPC ...... *H01L 29/0692* (2013.01); *H01L 29/1054* (2013.01); *H01L 29/66666* (2013.01)

(56) References Cited

U.S. PATENT DOCUMENTS

| | | | |
|---|---|---|---|
| 5,334,281 | A | 8/1994 | Doerre et al. |
| 5,431,883 | A | 7/1995 | Barraud |
| 5,683,569 | A | 11/1997 | Chung et al. |
| 6,111,280 | A | 8/2000 | Gardner et al. |
| 6,355,532 | B1 | 3/2002 | Seliskar et al. |
| 6,433,356 | B1 | 8/2002 | Cahen et al. |
| 6,437,404 | B1 | 8/2002 | Xiang et al. |
| 6,458,547 | B1 | 10/2002 | Bryan et al. |
| 6,753,200 | B2 | 6/2004 | Graighead et al. |
| 7,091,069 | B2 | 8/2006 | Doris et al. |
| 7,235,440 | B2 | 6/2007 | O'Meara et al. |
| 7,247,887 | B2 | 7/2007 | King et al. |
| 7,622,934 | B2 | 11/2009 | Hibbs et al. |
| 7,947,485 | B2 | 5/2011 | Wu et al. |
| 7,994,593 | B2 | 8/2011 | Takulapalli et al. |
| 8,154,093 | B2 | 4/2012 | Bradley et al. |
| 8,383,369 | B2 * | 2/2013 | Maxham .............. C12Q 1/6869 435/6.1 |
| 8,426,900 | B2 | 4/2013 | Ahn et al. |
| 9,170,228 | B2 | 10/2015 | Takulapalli |
| 9,341,592 | B2 * | 5/2016 | Takulapalli ........ G01N 27/4145 |
| 2002/0117659 | A1 | 8/2002 | Lieber et al. |
| 2003/0231531 | A1 | 12/2003 | Baxter |
| 2004/0043527 | A1 | 3/2004 | Bradley et al. |
| 2004/0079636 | A1 | 4/2004 | Hsia et al. |
| 2004/0132070 | A1 | 7/2004 | Star et al. |
| 2004/0144985 | A1 | 7/2004 | Zhang et al. |
| 2004/0195563 | A1 | 10/2004 | Bao et al. |
| 2004/0238379 | A1 | 12/2004 | Lindsay et al. |
| 2005/0026453 | A1 | 2/2005 | O'Meara et al. |
| 2005/0056892 | A1 | 3/2005 | Seliskar |
| 2005/0263790 | A1 | 12/2005 | Moon et al. |
| 2006/0113603 | A1 | 6/2006 | Currie |
| 2006/0154399 | A1 | 7/2006 | Sauer et al. |
| 2006/0243969 | A1 | 11/2006 | Bao et al. |
| 2006/0263255 | A1 | 11/2006 | Han et al. |
| 2006/0267051 | A1 | 11/2006 | Gstrein et al. |
| 2007/0063304 | A1 | 3/2007 | Matsumoto et al. |
| 2007/0108052 | A1 | 5/2007 | Luongo et al. |
| 2008/0063566 | A1 | 3/2008 | Matsumoto et al. |
| 2008/0081769 | A1 | 4/2008 | Hassibi |
| 2008/0094051 | A1 | 4/2008 | Williams et al. |
| 2008/0220530 | A1 | 9/2008 | Bahn et al. |
| 2008/0283875 | A1 | 11/2008 | Mukasa et al. |
| 2009/0014757 | A1 | 1/2009 | Takulapalli et al. |
| 2009/0273356 | A1 | 11/2009 | Pampin et al. |
| 2010/0066348 | A1 | 3/2010 | Merz et al. |
| 2010/0133107 | A1 | 6/2010 | Fishelson et al. |
| 2010/0237992 | A1 | 9/2010 | Liautaud |
| 2010/0297608 | A1 | 11/2010 | Stern et al. |
| 2010/0327255 | A1 | 12/2010 | Peng et al. |
| 2011/0024771 | A1 | 2/2011 | Hajj-Hassan et al. |
| 2011/0088466 | A1 | 4/2011 | Frerichs |
| 2011/0278258 | A1 | 11/2011 | Kavusi et al. |
| 2011/0279125 | A1 * | 11/2011 | Bedell .................. B82Y 15/00 324/444 |
| 2012/0021204 | A1 * | 1/2012 | Pei ....................... B81C 1/00087 428/314.2 |
| 2012/0045844 | A1 | 2/2012 | Rothberg et al. |
| 2012/0055236 | A1 | 3/2012 | Takulapalli |
| 2012/0094852 | A1 | 4/2012 | Berman et al. |
| 2012/0190989 | A1 | 7/2012 | Kaiser et al. |
| 2012/0131403 | A1 | 10/2012 | Cash et al. |
| 2012/0286330 | A1 | 11/2012 | Kellam |
| 2014/0327446 | A1 | 11/2014 | Bedell et al. |
| 2015/0060952 | A1 | 3/2015 | Takulapalli et al. |
| 2015/0376692 | A1 | 12/2015 | Esfandyarpour et al. |
| 2016/0041155 | A1 | 2/2016 | Takulapalli |
| 2016/0041159 | A1 | 2/2016 | Labaer et al. |
| 2019/0145950 | A1 | 5/2019 | Takulapalli |

FOREIGN PATENT DOCUMENTS

| | | |
|---|---|---|
| CN | 102242062 | 11/2011 |
| EP | 2836828 | 2/2015 |
| EP | 2973456 | 1/2016 |
| GB | 2389424 | 11/2004 |
| GB | 2416210 | 1/2006 |
| JP | 07333182 | 12/1995 |
| JP | 2004309483 | 11/2004 |
| JP | 2005061960 | 3/2005 |
| WO | 2005015193 | 2/2005 |
| WO | 2006134942 | 12/2006 |
| WO | 2009017882 | 2/2009 |
| WO | 2010026488 | 3/2010 |
| WO | 2011017077 | 2/2011 |
| WO | 2012075445 | 6/2012 |
| WO | 2012131403 | 10/2012 |
| WO | 2013063126 | 5/2013 |
| WO | 2013155116 | 10/2013 |
| WO | 2014143954 | 9/2014 |
| WO | 2014146020 | 9/2014 |
| WO | 2017184790 | 10/2017 |

OTHER PUBLICATIONS

International Preliminary Report on Patentability dated Dec. 11, 2009 in Application No. PCT/US2008/066190.
Office Action dated Sep. 13, 2010 in U.S. Appl. No. 12/135,940.
Notice of Allowance dated Mar. 31, 2011 in U.S. Appl. No. 12/135,940.
Office Action dated May 31, 2013 in Japanese Application No. 2010-511384.
International Search Report and Written Opinion dated Jul. 2, 2013 in Application No. PCT/US2013/035852.
Office Action dated Oct. 3, 2013 in U.S. Appl. No. 12/663,666.
Office Action dated Jan. 9, 2014 in Japanese Application No. 2010-511384.
Office Action dated Apr. 8, 2014 in U.S. Appl. No. 12/663,666.
Final Office Action dated Oct. 3, 2014 in Japanese Application No. 2010-511384.
International Preliminary Report on Patentability dated Oct. 14, 2014 in Application No. PCT/US2013/035852.
International Search Report and Written Opinion dated Nov. 12, 2014 in Application No. PCT/US2014/030891.
Notice of Allowance dated Jan. 22, 2015 in U.S. Appl. No. 12/663,666.
Office Action dated May 27, 2015 in U.S. Appl. No. 14/391,661.
Supplemental Notice of Allowability dated Jun. 3, 2015 in U.S. Appl. No. 12/663,666.
International Preliminary Report on Patentability dated Sep. 15, 2015 in Application No. PCT/US2014/030891.
Notice of Allowance dated Feb. 18, 2016 in U.S. Appl. No. 14/391,661.
Office Action dated Apr. 14, 2016 in Chinese Application No. 201380030209.6.
Extended European Search Report dated Oct. 19, 2016 in European Application No. 14762408.4.
Communication Pursuant to Article 94(3) EPC dated Jan. 27, 2017 in European Application No. 08826782.8.

(56) References Cited

OTHER PUBLICATIONS

Office Action dated Feb. 27, 2017 in Chinese Application No. 201380030209.6.
Ashcroft, et al., Calibration of a PH Sensitive Buried Channel Silicon-on-Insulator MOSFET for Sensor Applications, vol. 241, No. 10, Jul. 28, 2004, pp. 2291-2296.
Bouvet, Phthalocyanine-based field-effect transistors as gas sensors, Anal. Bioanal. Chem., 2006, vol. 384, pp. 366-373.
Hall, et al., GMR biosensor arrays: A system perspective, Biosensors and Bioelectronics, vol. 25, No. 9, May 15, 2010, pp. 2051-2057.
Langmuir-Blodgett deposition of Porphyrin molecules for sensing applications, 1 page.
Laws, Drain current control in a hybrid molecular/MOSFET device, Physica E 17, 2003, pp. 659-663.
Martinoia, et al., A behavioral macromodel of the ISFET in SPICE, Sensors and Actuators B, Elsevier Sequoia S. A., Lausanne, CH, vol. 62, No. 3, Mar. 1, 2000, pp. 182-189. ISSN: 0925-4005.
Ouisse, et al., Influence of series resistances and interface coupling on the transconductance of fully-depleted silicon-on-insulator MOSFETs, Solid-State Electronic, 1992, vol. 35, No. 2, pp. 141-149.
Shepherd, et al., Weak Inversion ISFETs for ultra-low power biochemical sensing and real-time analysis, Sensors and Actuators, Elsevier Sequoia S.A., Lausanne, CH, vol. 107, No. 1, May 27, 2005, pp. 468-473. ISSN: D0925-4005.
Suk, et al., "ZnO Nanorod Biosensor for Highly Sensitive Detection of Specic Protein Binding," Journal of the Korean Physical Society, vol. 49 No. 4, Oct. 1, 2006, retrieved from http://s-space.snu.ac.kr/bitstream/10371/5426/1/ZnO%20Nanorod%20Biosensor%20for%20Highly%20Sensitive%20Detection%20of%20Specific%20Protein%20Binding.pdf.
Takulapalli, Detection of Pyridine using ZnTCPP SAM Coated SOI Mosfet Devices, Jun. 9, 2006, 65 pages.
Takulapalli, Molecular Sensing Using Monolayer Gate Fully Depleted Silicon on Insulator Nano MOSFETS, Aug. 2006, 244 pages.
Takulapalli, Molecular Sensing Using Monolayer Floating Gate, Fully Depleted SOI MOSFET Acting as an Exponential Transucer, ACS Nano, Nov. 9, 2010, vol. 4, No. 2, pp. 999-1011.
Takulapalli, et al., The PH response of a silicon-on-insulator MOFSET with an integrated nanofluidic cell, In SOI Conference, 2003, IEE International, pp. 114-116.
Yang, et al., Controlling the threshold voltage of a metal-oxide-semiconductor field effect transistor by molecular protonation of the Si:SiO2 interface, J. Vac. Sci. Technol. B 20(4), Jul./Aug. 2002, pp. 1706-1709.
Yang, et al., Molecular Control of the Drain Current in a Buried Channel MOSFET, Sep. 2002, 4 pages.
Yang, et al., Molecular control of the threshold voltage of an NMOS inversion layer, Microelectronic Engineering, vol. 63, 2002, pp. 135-139.
USPTO; Requirement for Restriction dated May 24, 2018 in U.S. Appl. No. 14/777,425.
USPTO; Non-Final Office Action dated Sep. 7, 2018 in U.S. Appl. No. 14/777,425.
PCT; International Search Report dated Sep. 5, 2017 in International Application No. PCT/US2017/028468.
PCT; Written Opinion of the International Searching Authority dated Sep. 15, 2017 in International Application No. PCT/US2017/028468.
PCT; International Preliminary Report on Patentability dated Oct. 23, 2018 in International Application No. PCT/US2017/028468.
PCT; International Search Report dated Feb. 15, 2019 in International Application PCT/US2018/063170.
PCT; Written Opinion of the International Searching Authority dated Feb. 15, 2019 in International Application No. PCT/US2018/063170.

JPO; Final Examination Report dated Oct. 3, 2014 in Japanese Application No. 2010-511384.
CIPO; Notice of Allowance dated Aug. 2, 2017 in Chinese Application No. 201380030209.6.
CIPO; Examination Report dated Jul. 4, 2018 in Chinese Application No. 201480027713.5.
EPO; Supplementary Search Report dated Nov. 7, 2016 in European Application No. 14762408.4.
EPO; Examination Report dated Dec. 7, 2018 in European Application No. 14762408.4.
EPO; Examination Report dated Jan. 27, 2017 in European Application No. 08826782.8.
EPO; 2nd Examination Report dated Oct. 23, 2017 in European Application No. 08826782.8.
INPO; Examination Report dated Jun. 29, 2018 in Indian Application No. 9382/DELNP/2014.
Venkatesan et al., "Nanopore Sensors for Nucleic Acid Analysis," Nature Nanotechnology, vol. 6, pp. 615-624, (2011).
Reiner et al., "Disease Detection and Management Via Single Nanopore-Based Sensors," Chemical Reviews, vol. 112(12), pp. 6431-6451, (Dec. 2012).
Miles et al., "Single Molecule Sensing with Solid-State Nanopores: Novel Materials, Methods, and Applications," Chemical Society Reviews, vol. 42(1), pp. 15-28, (2013).
Storm et al., "Electron-Beam-Induced Deformations of SiO2 Nanostructures," Journal of Applied Physics, vol. 98, 014307 (8 Pages), (Jul. 2005).
Ishikawa et al.,"Fabrication of [110]-Aligned Si Quantum Wires Embedded in SiO2 by Low-Energy Oxygen Implantation," Nuclear Instruments and Methods in Physics Research, vol. 147, pp. 304-309, (1999).
Sano et al., "Immuno-PCR: Very Sensitive Antigen Detection by Means of Specific Antibody-DNA Conjugates," Science, vol. 258(5079), pp. 120-122, (1992).
Nam et al., "Nanoparticle-Based Bio-Bar Codes for the Ultrasensitive Detection of Proteins," Science, vol. 301(5641), pp. 1884-1886, (Sep. 2003).
Niemeyer et al., "Self-Assembly of DNA-Streptavidin Nanostructures and Their Use as Reagents in Immuno-PCR," Nucleic Acids Research, vol. 27(23), pp. 4553-4561, (1999).
Zhou et al., "Universal Immuno-PCR for Ultra-Sensitive Target Protein Detection," Nucleic Acids Research, vol. 21(25), pp. 6038-6039, (Dec. 1993).
Niemeyer et al., "Immuno-PCR: High Sensitivity Detection of Proteins by Nucleic Acid Amplification," Trends in Biotechnology, vol. 23(4), pp. 208-216, (Apr. 2005).
Crowther, "Enzyme Linked Immunosorbent Assay (ELISA)," Molecular Biomethods Handbook, Chapter 37, pp. 657-682, (2008).
Chang et al., "Immuno-PCR: An Ultrasensitive Immunoassay for Biomolecular Detection," Analytica Chimica Acta, vol. 910, pp. 12-24, (Mar. 2016).
Takulapalli et al., "Electrical Detection of Amine Ligation to a Metalloporphyrin via a Hybrid SOI-MOSFET," Journal of the American Chemical Society, vol. 130, pp. 2226-2233, (2008).
Takulapalli et al., "High Density Diffusion-Free Nanowell Arrays," Journal of Proteome Research, vol. 11, pp. 4382-4391, (2012).
Heath et al., "Single Cell Analytic Tools for Drug Discovery and Development," Nat Rev Drug Discovery, vol. 15(3), pp. 204-216, (Mar. 2016).
Oberleitner, "Thesis: Label-Free and Multi-Parametric Monitoring of Cell-Based Assays with Substrate-Embedded Sensors," Dissertation, University of Regensburg, (2015).
Barizuddin et al., "Plasmonic Sensors for Disease Detection—A Review," Journal of Nanomedicine and Nanotechnology, vol. 7(3), p. 1000373 (10 Pages), (2016).
Liu et al., "Super-Selective Cryogenic Etching for Sub-10 NM Features," Nanotechnology, vol. 24(1), p. 015305, (2013).
Zheng et al., "Frequency Domain Detection of Biomolecules using Silicon Nanowires Biosensors," Nano Letters, vol. 10(8), pp. 3179-3183, (Aug. 2010).

(56) References Cited

OTHER PUBLICATIONS

Kulkarni et al., "Detection Beyond the Debye Screening Length in a High-Frequency Nanoelectronic Biosensor," Nano Letters, vol. 12(2), pp. 719-723, (2012).
Abe et al., "Electrochemically Controlled Layer-by-Layer Deposition of Metal-Cluster Molecular Multilayers on Gold," Angewandte Chemie International Edition, vol. 42(25), pp. 2912-2915, (Jun. 2003).
Phanl et al., "Molecular Self-Assembly at Metal-Electrolyte Interfaces," International Journal of Molecular Sciences, vol. 14(3), pp. 4498-4524, (Mar. 2013).
Bischoffa et al., "Amino Acids: Chemistry, Functionality and Selected Non-Enzymatic Post-Translational Modifications," Journal of Proteomics, vol. 75(8), pp. 2275-2296, (Apr. 2012).
ThermoFisher, "Overview of Post-Translational Modifications (PTMs)," https://www.thermofisher.com/us/en/home/life-science/protein-biology/protein-biology-learning-center/protein-biology-resource-library/pierce-protein-methods/overview-post-translational-modification.html.
Robertson, "What is DNA Methylation?" News Medical Life Sciences, http://www.news-medical.et/life-sciences/What-is-DNA-Methylation.aspx.
"Histone Modifications: A Guide," abcam.com/epigenetics/histone-modification-a-guide, 8 Pages.
Rothbart et al., "Interpreting the Language of Histone and DNA Modifications," Biochim Biophys Acta, vol. 1839(8), pp. 627-643, (2014).
Breiling et al., "Epigenetic Regulatory Functions of DNA Modifications: 5-Methylcytosine and Beyond," Epigenetics & Chromatin, vol. 8(24), 9 Pages, (2015).
Feinberg et al., "Epigenetic Modulators, Modifiers and Mediators in Cancer Aetiology and Progression," Nature Reviews Genetics, vol. 17, pp. 284-299, (2016).
Baird et al., "Blood-Based Proteomic Biomarkers of Alzheimer's Disease Pathology," Frontiers in Neurology, vol. 6, Article 236, 16 Pages, (Nov. 2015).
Clark et al., "Advances in Blood-Based Protein Biomarkers for Alzheimer's Disease," Alzheimer's Research & Therapy, vol. 5(18), 8 Pages, (2013).

\* cited by examiner

FIELD EFFECT TRANSISTOR, DEVICE INCLUDING THE TRANSISTOR, AND METHODS OF FORMING AND USING SAME

CROSS REFERENCE TO RELATED APPLICATIONS

This application is a continuation of U.S. patent application Ser. No. 14/391,661, and filed on Oct. 9, 2014, entitled FIELD EFFECT TRANSISTOR, DEVICE INCLUDING THE TRANSISTOR, AND METHODS OF FORMING AND USING USE, which is the U.S. National Phase entry of International Application No. PCT/US2013/035852, filed on Apr. 9, 2013 and claims the benefit to U.S. Provisional Patent Application Ser. No. 61/621,966, entitled FIELD EFFECT NANOPORE DEVICE AND CHEMICAL-STOP NANOPORE ETCHING FOR GENOME SEQUENCING, PROTEIN SEQUENCING AND OTHER APPLICATIONS, and filed Apr. 9, 2012 and U.S. Provisional Patent Application Ser. No. 61/802,235, entitled FIELD EFFECT NANOPORE TRANSISTOR DEVICE METHODS OF FORMING AND USING THE SAME, and filed Mar. 15, 2013, the disclosures of which are incorporated herein by reference to the extent such disclosures do not conflict with the present disclosure.

GOVERNMENT LICENSE RIGHTS

This invention was made with government support under grant number 5R21HG006314 awarded by NIH. The United States government has certain rights in the invention.

FIELD OF THE INVENTION

The present invention generally relates to field effect transistors and devices including the transistors. More particularly, the invention relates to field-effect transistors suitable for detection of various materials, to devices including the transistors and to methods of forming and using the transistors and devices.

BACKGROUND OF THE INVENTION

Various sensors can be used to detect and characterize materials, such as biological, chemical, and/or radiological materials. For example, nanopore or nanochannel sensors have been developed to detects and characterize biological materials. In recent years, nanopore based sequencing approaches for detecting and characterizing biological materials have gained interest because such techniques offer two distinct advantages over other technology platforms, including: (i) point transduction capability and (ii) high speed nanopore translocation. Methods of nanopore based sequencing of biological material include: ion current blockade technique and more recently, transverse electron transport techniques. While these techniques hold promise to deliver a solution that is able to read-out the three billion base pairs at low cost and in a reasonably short period of time, they suffer from few fundamental limitations.

Ion current blockade techniques are limited by relatively low ion mobility in aqueous solution, when measuring ion-current across a nanopore. A recent study shows a current response over a time period of $10^4$ micro seconds for a step input applied and measured across a nanopore device, potentially limiting the rate of sequencing to below 1000 bases per second. Transverse electron transport measurements on the other hand are limited in sequencing-speed by quantum mechanical noise. In both ion current blockade and transverse electron transport techniques, these limitations result in failure to exploit the most significant advantage of high-speed DNA translocation in nanopore. Researchers have thus used methods to slow-down the DNA, from its natural high speed translocation of few million bases per second in solid state nanopores and up to 100 million bases per second in graphene nanopores.

A low cost, high quality solution to whole genome sequencing is generally desirable. Such a technology at low cost could lead to true personalized diagnostics and personalized therapeutics. Various technologies aim to provide just such a solution utilizing various technology approaches. However, such systems are generally expensive and therefore out of reach for many patients. Accordingly, a device and method where the total cost, cumulative of devices, instrumentation, reagents, time-cost and other resources, is relatively low, i.e., a desktop sequencer that will enable monitoring of mutations in a tumor over a period of time, and avails genome sequencing even to poorer countries, are desired.

SUMMARY OF THE INVENTION

The present invention provides an improved field effect transistor and device that can be used to sense and characterize a variety of materials. The field effect transistor and/or device including the transistor may be used for a variety of applications, including genome sequencing, protein sequencing, biomolecular sequencing, and detection of ions, molecules, chemicals, biomolecules, metal atoms, polymers, nanoparticles and the like. For example, the device can be used for detecting un-modified proteins, DNA and other biomolecules or proteins, DNA, biomolecules that have been modified with chemical tags or metal atom tags, nanoparticle tags, hybridization markers, or the like.

As set forth in more detail below, exemplary devices in accordance with various embodiments of the invention, take advantage of one or more of field effect transistor transduction mechanism and electric field focusing (e.g., at a bi-feature, e.g., conical or pyramidal sub-1000 nm to sub-10 nm nanopore). The field effect transistors and devices described herein can be operated in accumulation, depletion, partial depletion, full depletion, inversion or volume inversion mode.

In accordance with various embodiments of the disclosure, a device includes a substrate, an etch region formed within a portion of the substrate, an insulating region formed proximate the etch region, a source region overlying the insulating region and a first surface of the substrate, and a drain region formed overlying the insulating region and a second surface of the substrate. In accordance with various exemplary aspects of these embodiments, the device is capable of sensing and differentiating biological, chemical, and/or radiological species. The substrate may include conducting material, such as metal, semiconducting material, and/or insulating material. The device may include an additional semiconducting, metallic, or insulating layer proximate the insulating region. In accordance with further aspects, the substrate is selected from the group consisting of silicon, silicon on insulator, silicon on sapphire, silicon on silicon carbide, silicon on diamond, gallium nitride (GaN), GaN on insulator, gallium arsenide (GaAs), GaAs on insulator, germanium or germanium on insulator. In accordance with further aspects, the etch region includes a shape selected from the group comprising conical, pyramidal, spherical, or that has a cross section in the shape of a circle, rectangle, polygon, or slit. In accordance with yet further aspects of the disclosure, the device further includes a dielectric layer overlying a portion of the source region and/or the drain region. In accordance with yet further aspects, the device includes thin-film coating of material (e.g., organic, inorganic, or biological material) to facilitate detection of one or more chemical, biological, and/or radioactive materials. The thin-film coating may cover a portion of the device surface, such as the surface within the etch region. The device may include a nanopore, having a diameter of from about 1 nm to about 1000 nm, through the etch region.

In accordance with additional embodiments of the disclosure, a device includes an insulating substrate, an etch region formed within a portion of the insulating substrate, a layer formed of one or more of semiconducting, conducting, or topological insulating material formed overlying the insulating layer, a source region formed overlying the layer and a first surface of the substrate and a drain region formed overlying the layer and a second surface of the substrate. Various layers of devices in accordance with these embodiments may be formed of the same materials described above for the corresponding device layers. In accordance with yet further aspects, the device includes thin-film coating of material (e.g., organic, inorganic, or biological material) to facilitate detection of one or more chemical, biological, and/or radioactive materials. The thin-film coating may cover a portion of the device surface, such as the surface within the etch region. The device may include a nanopore, having a diameter of from about 1 nm to about 1000 nm, through the etch region.

In accordance with additional embodiments of the disclosure, a method of forming a device includes the steps of providing a substrate (e.g., a semiconductor, conductor, or insulator), etching a portion of the substrate to form an etch region, forming an insulating region proximate the etch region, forming a source region overlying the insulating region and a first surface of the substrate, and forming a drain region overlying the insulating region and a second surface of the substrate. In accordance with exemplary aspects of these embodiments, the step of providing a substrate includes providing a substrate comprising semiconductor material, such as silicon, silicon on insulator, silicon on sapphire, silicon on silicon carbide, silicon on diamond, gallium nitride (GaN), GaN on insulator, gallium arsenide (GaAs), GaAs on insulator, germanium or germanium on insulator. In accordance with further aspects, the step of forming an insulating region comprises one or more techniques selected from the group consisting of implantation (e.g., oxygen implantation), thermal oxidation, chemical vapor deposition, spin coating, vapor coating, spray coating, and dip coating. In accordance with further aspects, the step of etching includes etching along a crystalline plane of the substrate. Such etching may be self-limiting. The method may further include a step of annealing to obtain desired layer and/or device properties. In accordance with yet additional aspects of these embodiments, the method further includes the step(s) of forming a mask on the first surface and/or on the second surface within the etch region, which may be done using self-aligned technology. The method may further include the step of forming a nanopore (e.g., having a diameter between about 1 nm and 1000 nm) through the substrate. In accordance with various aspects of these embodiments, the nanopore is formed using one or more of: ion milling, electron beam milling, laser techniques; chemical stop wet etching, and wet etching. In accordance with yet additional aspects of these embodiments, the method may further include a step of depositing a semiconductor layer, metal layer, and/or a second insulating overlying the insulating layer. The method may further include forming at least one biological nanopore and/or chemical nanopore, which may be proximate a solid-state nanopore.

In accordance with additional embodiments of the disclosure, a method of forming a device includes the steps of providing a substrate (e.g., a semiconductor, conductor, or insulator), etching a portion of the substrate to form an etch region, and forming a layer selected from the group consisting of semiconducting layer, a metal layer, and a second insulating layer proximate the etch region. In accordance with various aspects of these embodiments, the method further comprises forming a source region overlying a first surface of the substrate and/or forming a drain region overlying a second surface of the substrate. In accordance with further aspects, the etching occurs along a crystalline plane of the substrate. The etching process may be self-limiting. In accordance with further aspects, the method includes an annealing step. The method may also include the step of forming a layer selected from the group consisting of semiconducting layer, a metal layer, and a second insulating layer proximate the etch region. The method may also include a step of forming a mask, which may be a self-aligned process. In accordance with further aspects, the method includes forming at least one nanopore though the substrate. The nanopore may be formed, for example, using one or more of ion milling, electron beam milling, laser, chemical stop wet etching, and wet etching. In accordance with further aspects, the method includes forming at least one lipid bilayer overlaying a nanopore. The method may further include forming at least one biological nanopore and/or chemical nanopore, which may be proximate a solid-state nanopore.

In accordance with yet further exemplary embodiments of the disclosure, a method of sensing material, such as chemical, biological, or radiological material (e.g., an ion, atom, or molecule) includes the steps of providing a device as described herein, providing material to be sensed, passing the material through a nanopore of the device; and detecting a variation in an electrical property of the device as the material passes through the nanopore. The material may be organic material, a nanoparticle, ionic species, molecular species, such as material selected from the group consisting of a DNA molecule, a protein molecule, a peptide molecule, a polypeptide molecule, an RNA molecule, a synthetic oligo nucleotide molecule, and a synthetic peptide or polypeptide molecule. The material to be sensed may be modified with at least one tag selected from the group consisting of metal species, metal-organic species, chemical modifiers, biomolecular tags, complementary hybridizing chain molecules, peptides, polypeptides, oligonucleotides, zinc fingers, nano particles, quantum dots, organic dyes, beads, nanowires, nanotubes.

BRIEF DESCRIPTION OF THE DRAWING FIGURES

The exemplary embodiments of the present invention will be described in connection with the appended drawing figures.

It will be appreciated that the figures are not necessarily drawn to scale. For example, the dimensions of some of the elements in the figures may be exaggerated relative to other elements to help to improve understanding of illustrated embodiments of the present invention.

DETAILED DESCRIPTION OF PREFERRED EMBODIMENTS OF THE INVENTION

The description of exemplary embodiments of the present disclosure provided below is merely exemplary and is intended for purposes of illustration only; the following description is not intended to limit the scope of the invention disclosed herein. Moreover, recitation of multiple embodiments having stated features is not intended to exclude other embodiments having additional features or other embodiments incorporating different combinations of the stated features.

Device Structure

Figure 1:
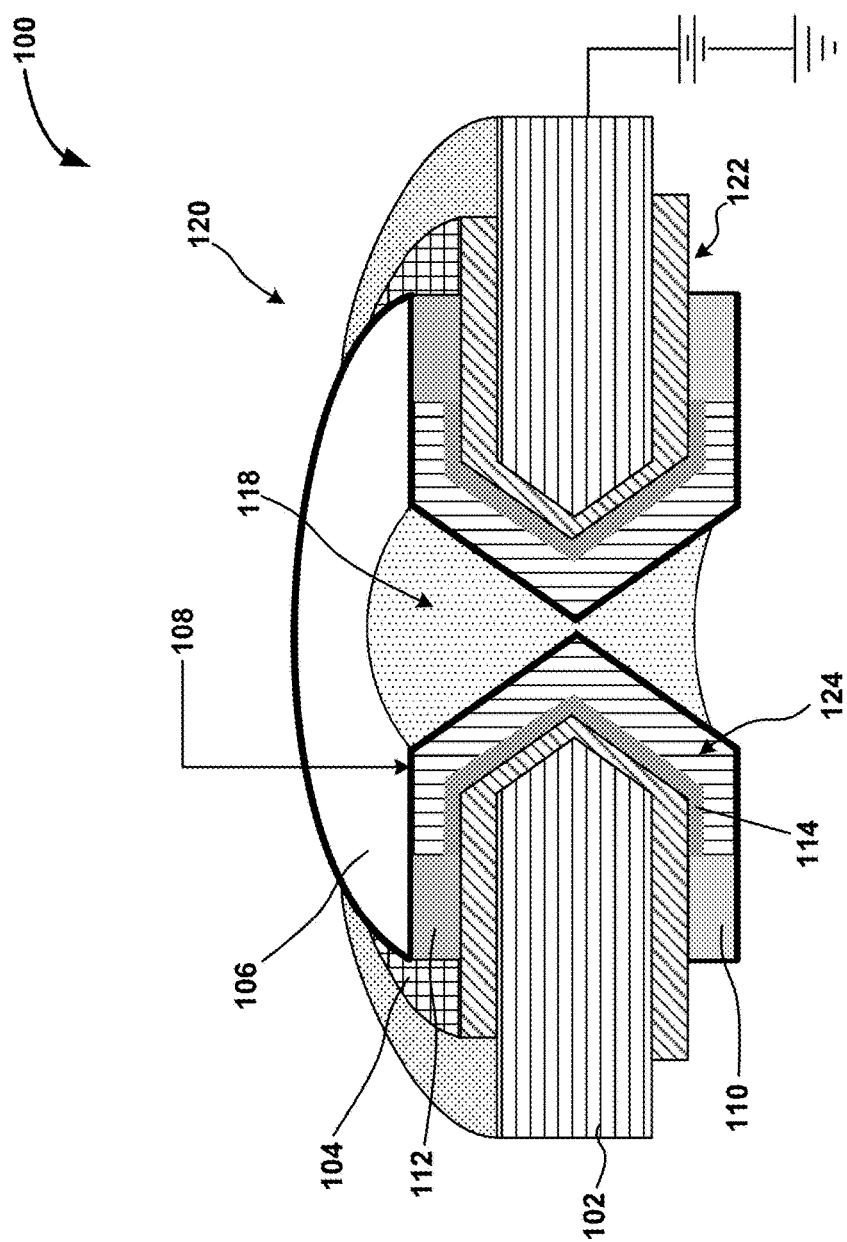
FIG. 1 illustrates a field effect transistor device in accordance with exemplary embodiments of the disclosure.

FIG. 1 illustrates a device 100 in accordance with various exemplary embodiments of the disclosure. Device 100 includes a substrate 102, an etch region 118 formed within a portion of substrate 102, an insulating region 104 formed proximate etch region 118, a source region 112 overlying insulating region 104 and a first surface 120 of substrate 102, and a drain region 110 formed overlying insulating region 104 and a second surface 122 of substrate 102. As illustrated, source region 112 and drain region 110 may be formed using layer 106. Device 100 may additionally include a dielectric layer 108. A width of the device 100 can be from 1 angstrom to about 10 millimeter or more.

As used herein, overlying is not restricted to meaning that a layer overlying another layer must be immediately adjacent the other layer. Various layers may be interposed between a substrate or layer and another layer overlying the substrate or layer. For example, in the illustrated device, layer 104 overlies substrate 102, layer 106 overlies layer 104 and substrate 102, and layer 108 overlies layer 106, layer 104, and substrate 102. Further, as used herein, a first surface and a second surface are not on a same side (e.g., top or bottom) of a structure or device, and in the illustrated examples are on opposite sides—top and bottom—of a substrate/device.

Substrate 102 may be formed of a variety of materials. For example, substrate 102 may include buried semiconductor material or a metal layer. Examples of substrate 102 material include, but are not limited to, semiconductors and metals, including silicon, germanium, graphene, diamond, tin or compound semiconductors like silicon carbide, silicon germanium, diamond, graphite, binary materials like aluminium antimonide (AlSb), aluminium arsenide (AlAs), aluminium nitride (AlN), aluminium phosphide (AlP), boron nitride (BN), boron phosphide (BP), boron arsenide (BAs), gallium antimonide (GaSb), gallium arsenide (GaAs), gallium nitride (GaN), gallium phosphide (GaP), indium antimonide (InSb), indium arsenide (InAs), indium nitride (InN), indium phosphide (InP), cadmium selenide (CdSe), cadmium sulfide (CdS), cadmium telluride (CdTe), zinc oxide (ZnO), zinc selenide (ZnSe), zinc sulfide (ZnS), zinc telluride (ZnTe), cuprous chloride (CuCl), lead selenide (PbSe), lead sulfide (PbS), lead telluride (PbTe), tin sulfide (SnS), tin telluride (SnTe), bismuth telluride (Bi2Te3), cadmium phosphide (Cd3P2), cadmium arsenide (Cd3As2), cadmium antimonide (Cd3Sb2), zinc phosphide (Zn3P2), zinc arsenide (Zn3As2), zinc antimonide (Zn3Sb2), other binary materials like lead(II) iodide (PbI2), molybdenum disulfide (MoS2), gallium Selenide (GaSe), tin sulfide (SnS), bismuth Sulfide (Bi2S3), platinum silicide (PtSi), bismuth(III) iodide (BiI3), mercury(II) iodide (HgI2), thallium(I) bromide (TlBr), semiconducting oxides like zinc oxide, titanium dioxide (TiO2), copper(I) oxide (Cu2O), copper(II) oxide (CuO), uranium dioxide (UO2), uranium trioxide (UO3), 6.1 Å materials, or ternary materials like aluminium gallium arsenide (AlGaAs, AlxGa1—xAs), indium gallium arsenide (InGaAs, InxGa1—xAs), aluminium indium arsenide (AlInAs), aluminium indium antimonide (AlInSb), gallium arsenide nitride (GaAsN), gallium arsenide phosphide (GaAsP), aluminium gallium nitride (AlGaN), aluminium gallium phosphide (AlGaP), indium gallium nitride (InGaN), indium arsenide antimonide (InAsSb), indium gallium antimonide (InGaSb), cadmium zinc telluride (CdZnTe, CZT), mercury cadmium telluride (HgCdTe), mercury zinc telluride (HgZnTe), mercury zinc selenide (HgZnSe), lead tin telluride (PbSnTe), thallium tin telluride (Tl2SnTe5), thallium germanium telluride (Tl2GeTe5) and quaternary like aluminium gallium indium phosphide (AlGaInP, InAlGaP, InGaAlP, AlInGaP), aluminium gallium arsenide phosphide (AlGaAsP), indium gallium arsenide phosphide (InGaAsP), aluminium indium arsenide phosphide (AlInAsP), aluminium gallium arsenide nitride (AlGaAsN), indium gallium arsenide nitride (InGaAsN), indium aluminium arsenide nitride (InAlAsN), copper indium gallium selenide (CIGS), or quinary materials like gallium indium nitride arsenide antimonide (GaInNAsSb), Mg, Al, Sc, Ti, V, Cr, Mn, Fe, Co, Ni, Cu, Zn, Ga, Y, Zr, Nb, Mo, Ru, Rh, Pd, Ag, La, Hf, Ta, W, Re, Os, Ir, Pt, Au, TaTi, Ru, HfN, TiN, and the like. Substrate 102 may include inorganic or organic semiconducting material as described in more detail below in connection with layer 106. In accordance with exemplary embodiments of the disclosure, substrate 102 is used as a gate to modulate conductivity of channel in layer 106. In accordance with these embodiments, substrate 102 may include, for example, an elemental or compound semiconductor, a metal, a metal alloy, a metal-semiconductor alloy, a semi metal, or any other organic or inorganic material suitable for use as a metal-oxide-semiconductor field-effect transistor (MOSFET) gate. This layer can be of any suitable thickness. In flexible devices this layer includes a flexible substrate, such as, for example an organic material like pentacene.

Insulating region 104 may be formed of any suitable insulating material. In accordance with exemplary aspects of various exemplary embodiments of the disclosure, region 104 is a gate insulator or gate dielectric layer suitable for establishing inversion, depletion or accumulation in a channel region of layer 106.

Inversion, depletion, or accumulation in layer 106 can be established using substrate bias or solution bias or portions of layer 106 can be inverted, depleted, or accumulated, without application of an external bias. Insulating region 104 can be made of any suitable organic or inorganic insulating material. Examples include, but are not limited to, silicon dioxide, silicon nitride, hafnium oxide, alumina, magnesium oxide, zirconium oxide, zirconium silicate, calcium oxide, tantalum oxide, lanthanum oxide, titanium oxide, yttrium oxide, titanium nitride, and the like. By way of one example, region 104 is formed using a buried oxide layer obtained using a oxygen implantation or SIMOX process. The thickness of this layer can be from, for example, about 1 nm to 100 microns or up to 1 mm or more.

In the illustrated example, source region 112 and drain region 110 are formed using layer 106, which may form a semiconductor channel thin film. By way of one example, layer 106 includes crystalline silicon film. Layer 106 may include, for example, crystalline or amorphous inorganic semiconductor material, such as those used in the regular MOS technologies. Exemplary materials include, but are not limited to, elemental semiconductors like silicon, germanium, graphene, diamond, tin or compound semiconductors like silicon carbide, silicon germanium, diamond, graphite, binary materials like aluminium antimonide (AlSb), aluminium arsenide (AlAs), aluminium nitride (AlN), aluminium phosphide (AlP), boron nitride (BN), boron phosphide (BP), boron arsenide (BAs), gallium antimonide (GaSb), gallium arsenide (GaAs), gallium nitride (GaN), gallium phosphide (GaP), indium antimonide (InSb), indium arsenide (InAs), indium nitride (InN), indium phosphide (InP), cadmium selenide (CdSe), cadmium sulfide (CdS), cadmium telluride (CdTe), zinc oxide (ZnO), zinc selenide (ZnSe), zinc sulfide (ZnS), zinc telluride (ZnTe), cuprous chloride (CuCl), lead selenide (PbSe), lead sulfide (PbS), lead telluride (PbTe), tin sulfide (SnS), tin telluride (SnTe), bismuth telluride (Bi2Te3), cadmium phosphide (Cd3P2), cadmium arsenide (Cd3As2), cadmium antimonide (Cd3Sb2), zinc phosphide (Zn3P2), zinc arsenide (Zn3As2), zinc antimonide (Zn3Sb2), other binary materials like lead (II) iodide (PbI2), molybdenum disulfide (MoS2), gallium Selenide (GaSe), tin sulfide (SnS), bismuth Sulfide (Bi2S3), platinum silicide (PtSi), bismuth(III) iodide (Bi13), mercury (II) iodide (Hg12), thallium(I) bromide (TlBr), semiconducting oxides like zinc oxide, titanium dioxide (TiO2), copper(I) oxide (Cu2O), copper(II) oxide (CuO), uranium dioxide (UO2), uranium trioxide (UO3), 6.1 Å materials, or ternary materials like aluminium gallium arsenide (AlGaAs, AlxGa1—xAs), indium gallium arsenide (InGaAs, InxGa1—xAs), aluminium indium arsenide (AlInAs), aluminium indium antimonide (AlInSb), gallium arsenide nitride (GaAsN), gallium arsenide phosphide (GaAsP), aluminium gallium nitride (AlGaN), aluminium gallium phosphide (AlGaP), indium gallium nitride (InGaN), indium arsenide antimonide (InAsSb), indium gallium antimonide (InGaSb), cadmium zinc telluride (CdZnTe, CZT), mercury cadmium telluride (HgCdTe), mercury zinc telluride (HgZnTe), mercury zinc selenide (HgZnSe), lead tin telluride (PbSnTe), thallium tin telluride (Tl2SnTe5), thallium germanium telluride (Tl2GeTe5) and quaternary like aluminium gallium indium phosphide (AlGaInP, InAlGaP, InGaAlP, AlInGaP), aluminium gallium arsenide phosphide (AlGaAsP), indium gallium arsenide phosphide (InGaAsP), aluminium indium arsenide phosphide (AlInAsP), aluminium gallium arsenide nitride (AlGaAsN), indium gallium arsenide nitride (InGaAsN), indium aluminium arsenide nitride (InAlAsN), copper indium gallium selenide (CIGS), or quinary materials like gallium indium nitride arsenide antimonide (GaInNAsSb), and the like.

Layer 106 can also be made of organic semiconducting materials. Examples of such materials include, but are not limited to, polyacetylene, polypyrrole, polyaniline, Rubrene, Phthalocyanine, Poly(3-hexylthiophene, Poly(3-alkylthiophene), α-ω-hexathiophene, Pentacene, α-ω-di-hexyl-hexathiophene, α-ω-dihexyl-hexathiophene, Poly(3-hexylthiophene), Bis(dithienothiophene, α-ω-dihexyl-quaterthiophene, Dihexyl-anthradithiophene, n-decapentafluoroheptylmethylnaphthalene-1,4,5,8-tetracarboxylic diimide, α-ω-dihexyl-quinquethiophene, N,N'-dioctyl-3,4,9,10-perylene tetracarbozylic, CuPc, Methanofullerene, [6,6]-phenyl-C61-butyric acid methyl ester (PCBM), C60, 3',4'-dibutyl-5-5bis(dicyanomethylene)-5,5'-dihydro-2,2',5',2" terthiophene (DCMT), PTCDI-C5, P3HT, Poly(3,3"-dialkyl-terthiophene), C60-fused N-methylpyrrolidine-meta-C12 phenyl (C60MC12), Thieno[2,3-b]thiophene, PVT, QM3T, DFH-nT, DFHCO-4TCO, BBB, FTTTTF, PPy, DPI-CN, NTCDI, F8T2-poly[9,9' dioctyl-fluorene-co-bithiophene], MDMO-PPV-poly[2-methoxy-5-(3,7-dimethyloctyloxy)]-1,4-phenylenevinylene, P3HT-regioregular poly[3-hexylthiophene]; PTAA, polytriarylamine, PVT-poly-[2,5-thienylene vinylene], DH-5T-α,ω-Dihexylquinquethiophene, DH-6T-α,ω-dihexylsexithiophene, phthalocyanine, α-6T-α-sexithiophene, NDI, naphthalenediimide, F16CuPc-perfluorocopperphthalocyanine, perylene, PTCDA-3,4,9,10-perylene-tetracarboxylic dianhydrid and its derivaties, PDI-N,N'-dimethyl 3,4,9,10-perylene tetracarboxylicdiimide, and the like.

Layer 106 may include topological insulator materials such as bismuth antimonide, pure antimony, bismuth selenide, bismuth telluride, antimony telluride, or alternate topological insulator materials known to those familiar with the field of invention.

An inversion channel 114 may be formed at a layer 106-layer 104 interface by controlling a voltage bias applied to substrate 102, or to a biasing the solution, or both. It is also possible that the inversion channel is formed in layer 106 with no external bias applied to substrate 102, depending on a doping level in layer 106, thickness of layer 106, other such variables, and, for example, a fixed oxide charge density and interface trap states density at its boundaries. The thickness of layer 106 can be from, for example, about 1 nm to 50 microns, depending on the material (e.g., semiconductor material) and its doping density. When biasing substrate 102 to obtain an inversion channel in layer 106, in one example case, the thickness (t) of layer 106 should be such that the whole thickness of layer 106 should be fully depleted before the formation of inversion channel at layer 106-layer 104 interface. In another example layer 106 is made very thin, so that it is operated in volume inversion mode. In another example layer 106 is operated in partial depletion mode. In yet another example case layer 106 is operated in depletion mode. In another example case layer 106 is operated in accumulation mode.

Layer 106 may include intrinsic or p-type or n-type doped material; correspondingly device 100 can be an n-channel device or a p-channel device, respectively. In exemplary cases, delta doping or implant doping of layer is used. Source region 112 and drain region 110 are formed on either side of the semiconductor layer 106 using known doping techniques.

One exemplary layer 106 includes 1 E15 doped p-type silicon layer of thickness between about 10 nm and about 1000 nm. In this case, an inversion layer is formed in the silicon thin film at a silicon (substrate 102)-buried oxide (layer 104) interface by biasing substrate 102. Alternatively, an accumulation layer may be formed at this interface. Or, volume inversion, accumulation may be formed in layer 106 which may be made less than 100 nm thin. In another example case inversion or accumulation are formed at the top surface of layer 106, at the layer 106-layer 108 interface, if present. Exemplary source and drain regions 112, 110 are 1 E 19 phosphorous doped N++ regions in this p-type Si channel.

Layer 108 may include any suitable dielectric material. A thickness of layer 108 may be between about 2 angstroms and 100 nm. Exemplary materials suitable for layer 108 include inorganic dielectric material that act as a gate dielectric material. Examples include, but not limited to, $SiO_2$, $Si_3N_4$, $SiN_x$, $Al_2O_3$, $AlO_x$ $La_2O_3$, $Y_2O_3$, $ZrO_2$, $Ta_2O_5$, $HfO_2$, $HfSiO_4$, $HfO_x$, $TiO_2$, $TiO_x$, a-$LaAlO_3$, $SrTiO_3$, $Ta_2O_5$, $ZrSiO_4$, $BaO$, $CaO$, $MgO$, $SrO$, $BaTiO_3$, $Sc_2O_3$, $Pr_2O_3$, $Gd_2O_3$, $Lu_2O_3$, $TiN$, $CeO_2$, BZT, BST or a stacked or a mixed composition of these and such other gate dielectric material.

Alternatively, layer 108 may include organic monolayers or other gate dielectric materials. Examples include, but are not limited to, PVP—poly (4-vinyl phenol), PS—polystyrene, PMMA—polymethyl-methacrylate, PVA—polyvinyl alcohol, PVC—polyvinylchloride, PVDF—polyvinylidenfluoride, PαMS—poly[α-methylstyrene], CYEPL—cyanoethylpullulan, BCB—divinyltetramethyldisiloxane-bis(benzocyclobutene), CPVP-Cn, CPS-Cn, PVP-CL, PVP-CP, polynorb, GR, nano $TiO_2$, OTS, Pho-OTS, various self-assembled monolayers or multilayers or a stacked or a mixed composition of these and such other gate dielectric material.

Layer 108 can also be made of topological insulator materials such as bismuth antimonide, pure antimony, bismuth selenide, bismuth telluride, antimony telluride, or alternate topological insulator materials known to those familiar with the field of invention.

Figure 2:
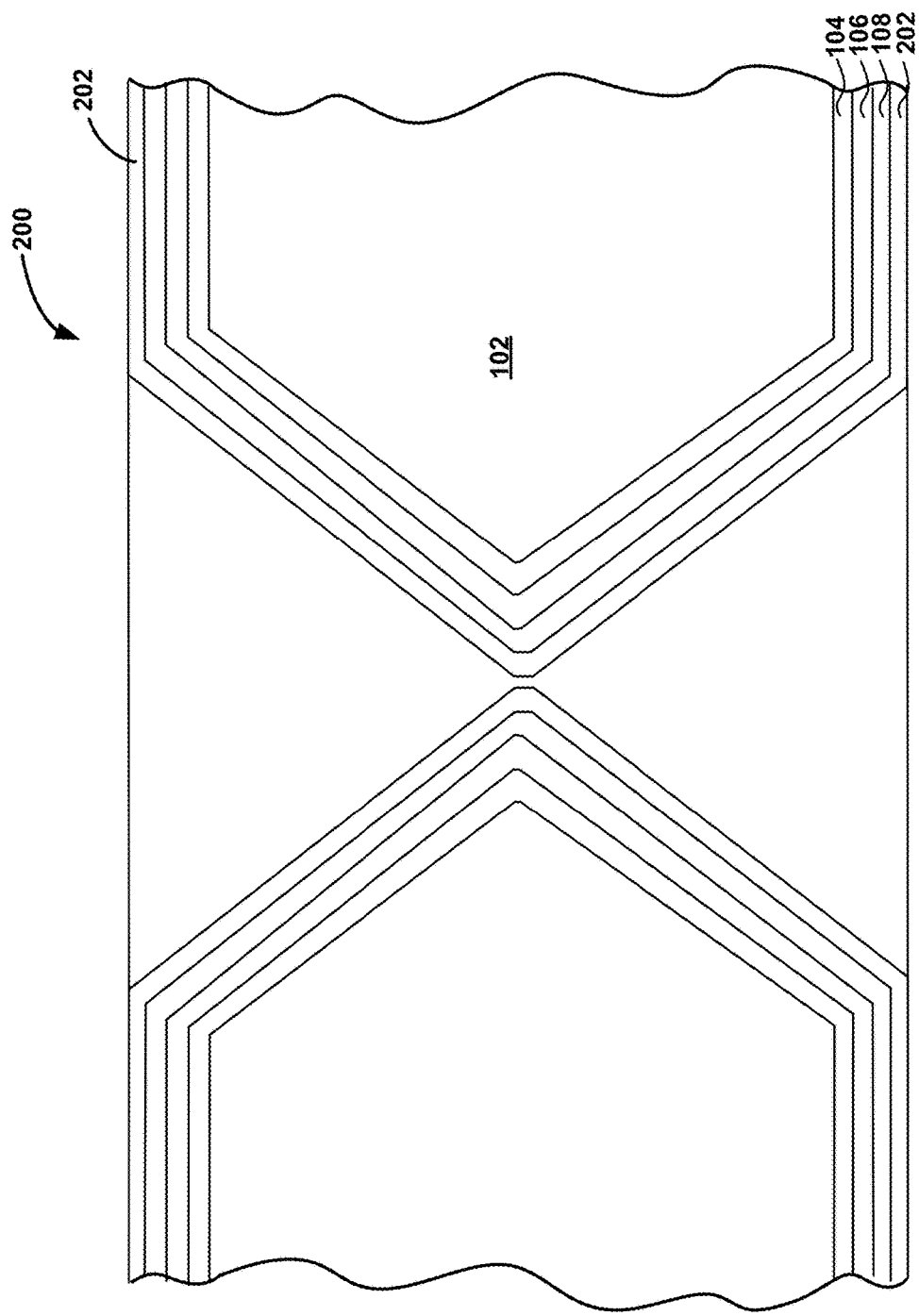
FIG. 2 illustrates another exemplary field effect transistor device in accordance with exemplary embodiments of the disclosure.

Turning now to FIG. 2, a device 200 is illustrated, Device 200 is similar to device 100, except device 200 includes an additional layer 202 overlying substrate 102 and layers 104-108.

Layer 202 may include material to additionally functionalize device 200. Layer 202 may be, for example, a thin film that is of thickness between 2 angstroms and 100 nm. Although illustrated as a single layer, layer 202 can be a combination of different layers of thin films of different materials. Layer 202 may include, for example, monolayer or multilayer of organic molecules or biomolecules; thin films of semiconducting materials, metals, semi metals, insulators, dielectric materials, meta-materials, or the like that may be additionally used to functionalize the device.

Alternately, layer 202 may include multilayers, where first layer is a thin film of one or more materials described above, and a second layer that is made with biological nano or micro pore molecules such as protein nanopore, alpha hemolysin, beta barrel, or DNA base nanopores or other biological or organic molecule based nanopore or micro pores. An exemplary case of layer 202 is when biological nanopore molecule is placed directly on top on layer 106 or layer 108. Layer 202 may include at least one lipid bilayer overlaying a nanopore or chemical nanopore material. When a device does not include a chemical or biological nanopore material, the device is referred to as a solid-state device, and when the device includes a chemical or biological material, the devices is referred to as a chemical nanopore device or a biological nanopore device.

Layer 108 and layer 202 can be deposited using any of the thin film fabrication techniques like sputtering, chemical vapor deposition, physical vapor deposition, epitaxy, atomic layer deposition (ALD), molecular beam epitaxy, e-beam thermal deposition, thermal deposition of other kinds, or any other deposition techniques for thin films or chemical deposition methods of single molecule monolayers or multilayers.

Figure 9:
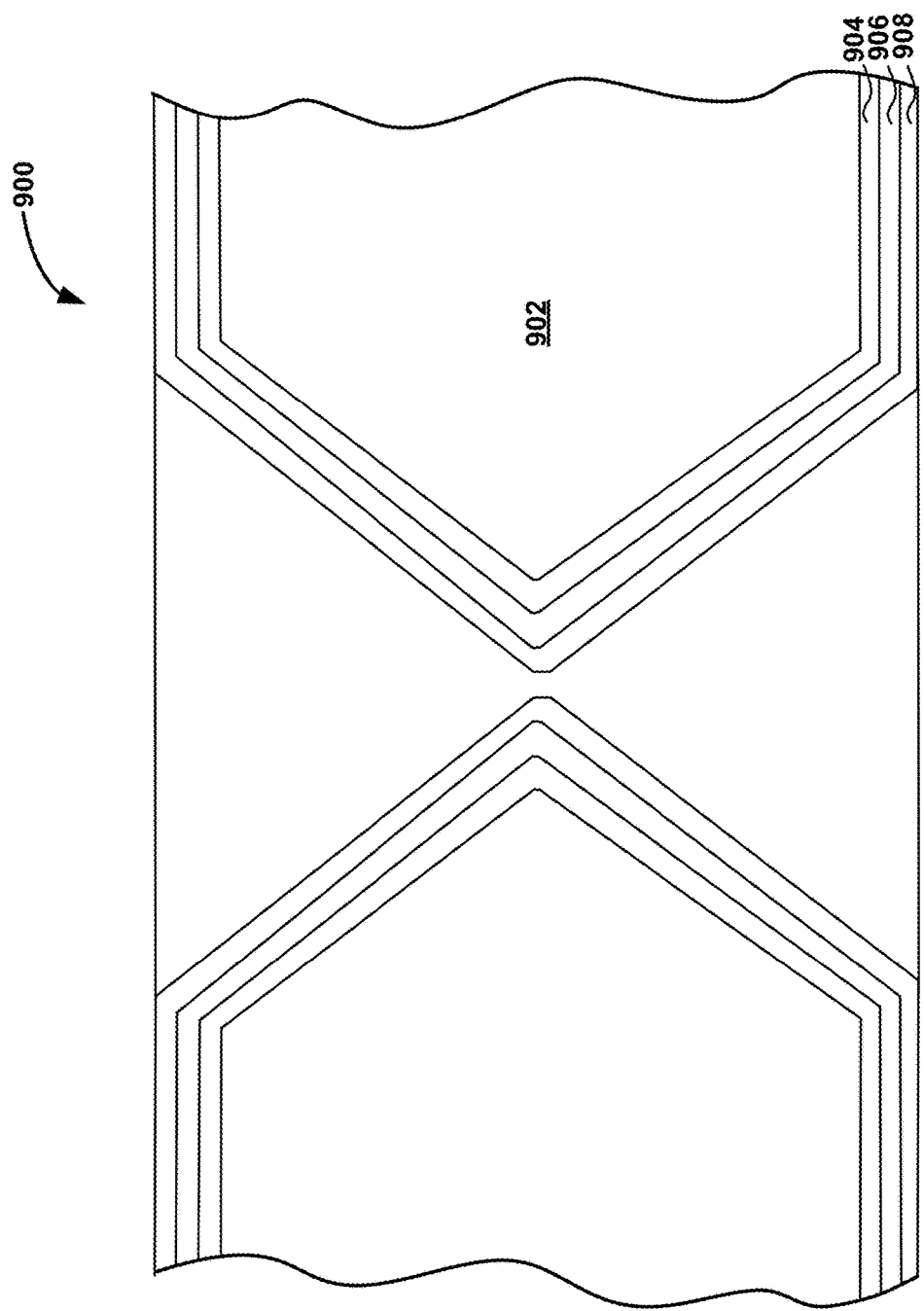
FIG. 9 illustrates another exemplary field effect transistor device in accordance with exemplary embodiments of the disclosure.

FIGS. 1 and 2 illustrate exemplary devices 100 and 200. Additional exemplary devices are similar to devices 100 and 200, except such devices do not include layer 108. Yet another alternative device 900 is illustrated in FIG. 9. Device 900 is similar to device 100 and 200, except device 900 includes insulating substrate 902 (which may include any of the materials described above in connection with layer 104), and layer 904-908 overly substrate 902. Layers 904-908 may correspond to layers 106-202, respectively.

As set forth above, devices in accordance with various embodiments of the invention may be formed using a variety of materials for the different device layers. The following non-limiting examples illustrate exemplary devices and methods of forming and using the devices in accordance with various embodiments of the disclosure. These examples are merely illustrative, and it is not intended that the invention be limited to the examples. Device in accordance with the present invention may include the compounds and materials listed below as well as additional and/or alternative materials noted herein.

SOI Device Structure:

In accordance with exemplary embodiments of the disclosure, a device is fabricated on silicon or silicon on insulator (SOI) wafers. Alternately devices in accordance with various embodiments can be fabricated on any semiconductor or semiconductor-on-insulator materials such as GaAS or GaAs on insulator or GaN or GaN on insulator, or other material, as noted above.

With reference to FIGS. 1 and 2, a device, such as device 100 or 200, in accordance with these exemplary embodiments, includes a semiconductor channel 124 that is continuous from source region 112 to drain region 110 and which narrows down into a bi-feature point nanopore through substrate 102 at the center. In this case, a silicon gate (in substrate 102), which acts as a back/buried-gate, is separated from semiconducting nanopore channel 124 by insulating region 104, which, in this example, is a gate oxide layer. Source region 112 and drain region 110, which are n+ doped in this example, may be connected to external instrumentation via bonding pads (e.g., gold) (not shown in schematic). When bias potential is applied to the silicon back-gate of the nanopore transistor, the gate oxide-silicon channel interface is driven into depletion first, followed by full-depletion of the thin film silicon, and then into inversion at the oxide-silicon interface. Inversion channel 114 formed is about 20 nm thin and is continuous along the oxide-silicon interface, from the circular disc of the source through the bi-feature-point-nanopore to the circular disc of the drain. Alternately an accumulation channel may be formed at the gate oxide-silicon channel interface. Or, inversion or accumulation channels may be formed at the top surface of layer 106. Drain current is measured across the source drain contacts and the devices may be operated at high frequencies from kilo hertz to megahertz to Giga hertz switching (speed is generally inversely proportional to gate oxide thickness).

Thus, measurements of individual molecular translocation events up-to and above 100,000 events per second may be obtained using these devise.

Electric Field Focusing and Coupling Amplification:

At the nanopore point location electric field focusing occurs due to feature curvature convoluted around the nanopore center. It is verified theoretically and experimentally that electrostatic field varies directly with surface curvature of an object, and electrostatic field extrema along an equipotential contour correspond to curvature extrema. And in specific case of 3D feature (e.g., conical or pyramidal) geometry field intensity characteristics approach a singularity with not just field intensity extrema but surface charge, potential, density of state and surface state interaction extrema occurring at such feature point geometries. In the exemplary MOSFET devices, electric field focusing is even more extreme due to the nano scale surface convoluted around the nanopore center. These amplified fields, states and interactions at the point nanopore location are then coupled to the exponentially transducing FET device structure. The response resulting from these double amplification events is read at above kilo/Megahertz frequencies via source-drain inversion channel current. While the simulations below illustrate a perfect bi-conical nanopore, this is only an exemplary case, and the device may have a single feature nanopore or an imperfect bi-feature (e.g., conical or pyramidal) nanopore.

Device Performance Characteristics & Simulation

Figure 7:
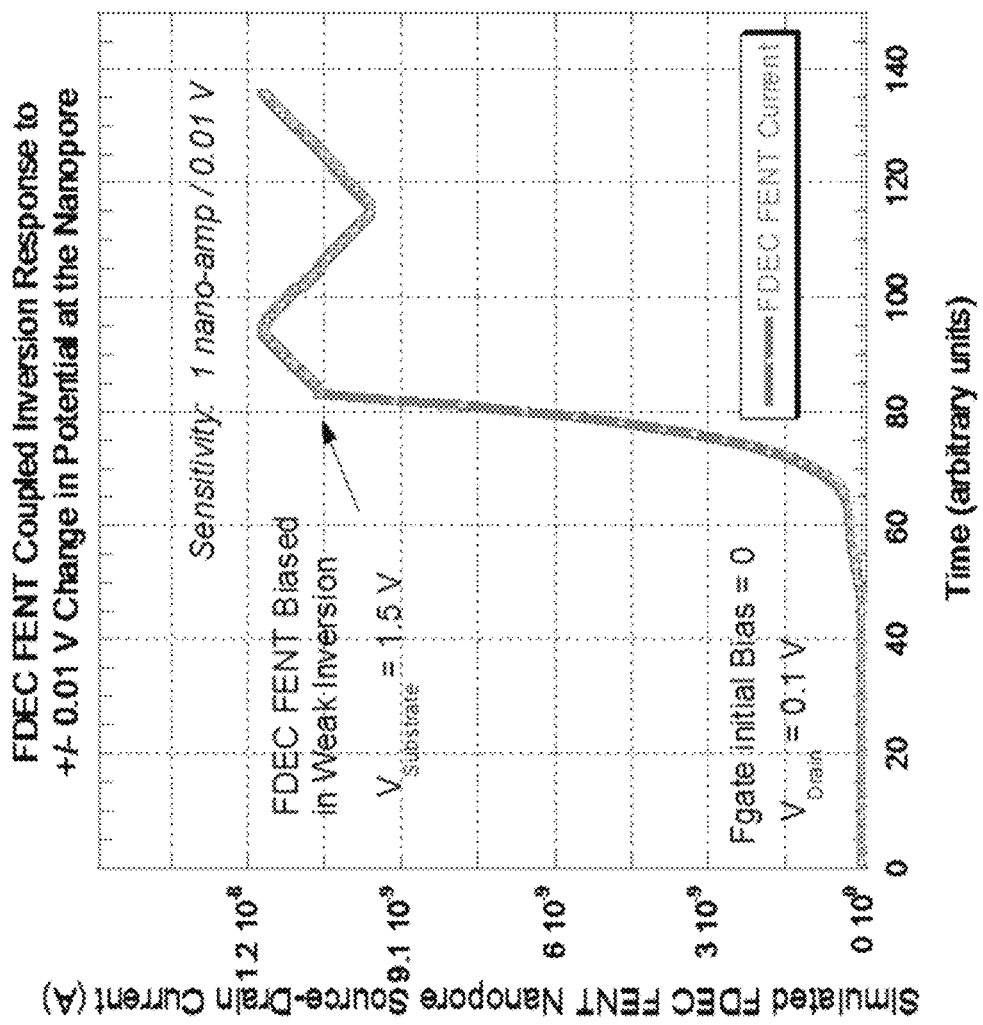
FIG. 7 illustrates a simulation of one nano-ampere inversion current response to 0.01 V variation in floating gate (nanopore) potential.

In exemplary devices, frequency of nanopore-potential coupling is generally related to thin dielectric film (high capacitance) and fully depleted silicon film thickness (design variable). 1/f noise is not a problem at these high frequencies. To validate device response to nanopore-potential variation, we performed preliminary 2D simulations using ATLAS (Silvaco) software. An 8 nm FET nanopore device is defined to scale—using tools available in Atlas. DNA Translocation is modeled by varying potential applied to FGate (Floating gate at nanopore center), and FET device response is simulated. FIG. 7 shows 1 nano-ampere inversion current response to 0.01 V variation in floating gate (nanopore) potential. SIMOX (separation of substrate 102 and layer 106 by implantation of oxygen) MOSFETs exhibit good sub-threshold characteristics even in ionic buffer solutions, with currents in pico ampere range. Hence nano-ampere inversion response results in noise ratios as high as 100. A sub-milli volt (to micro-volt) potential variation (mimicking an AC signal on a DC bias) due to DNA base translocation, coupled by other chemical or biological methods described herein, will be amplified first by field-focusing at the bi-feature nanopore, which is then exponentially coupled to inversion (or accumulation channel) channel-producing tens of picoampere to a few nanoampere range inversion current variation which is readily readable with high signal to noise ratios, enabling potential fast sequencing of DNA. Further, redundancy of device response for high quality sequencing is achieved by redundant combinatorial detection arrays based on complementary CMOS technology.

Exemplary Methods of Fabrication:

Chemical-Stop Nanopore Etching for Controlled Nanopore Diameter (10 nm to 1 nm)

Figure 3:
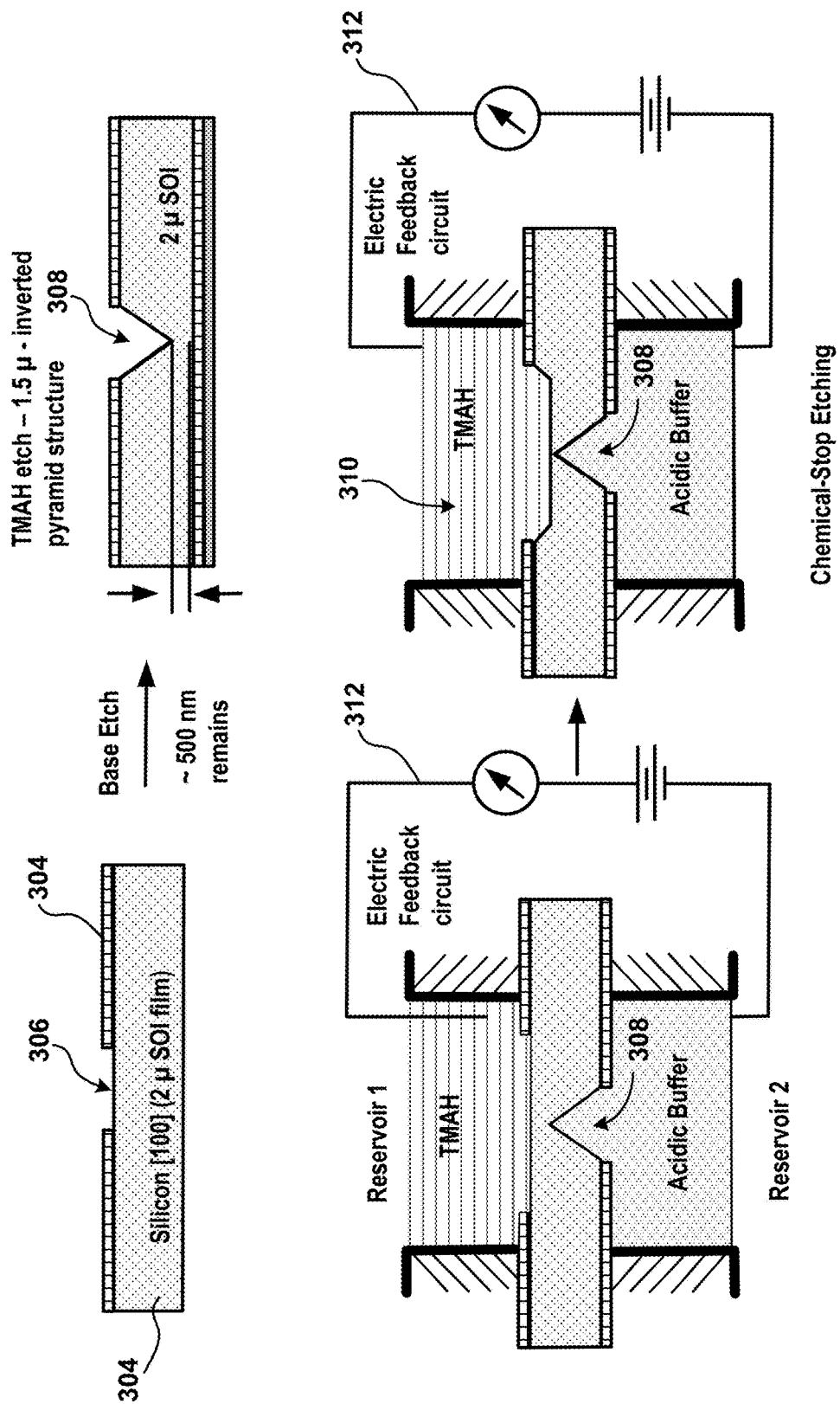
FIG. 3 illustrates steps of forming a field effect transistor device in accordance with exemplary embodiments of the disclosure.

Fabrication of nanopores in silicon by chemical etching using KOH and KCl with electrical feedback has been demonstrated to yield nanopores of controlled diameter. FIG. 3 illustrates an improved, nanopore fabrication process for precise control of nanopore diameter—e.g., for forming etch region 118. Etched region may be formed on one or both sides of the substrate layer. In the illustrated example, a silicon substrate 302 is masked with an e.g., a silicon nitride mask 304 (e.g., about 200 nm), having an opening 306 therein. The masked substrate is then exposed to a first etch solution to form an etch region 308. The structure is then exposed to a second etch solution to form second etch region 310.

Figure 6:
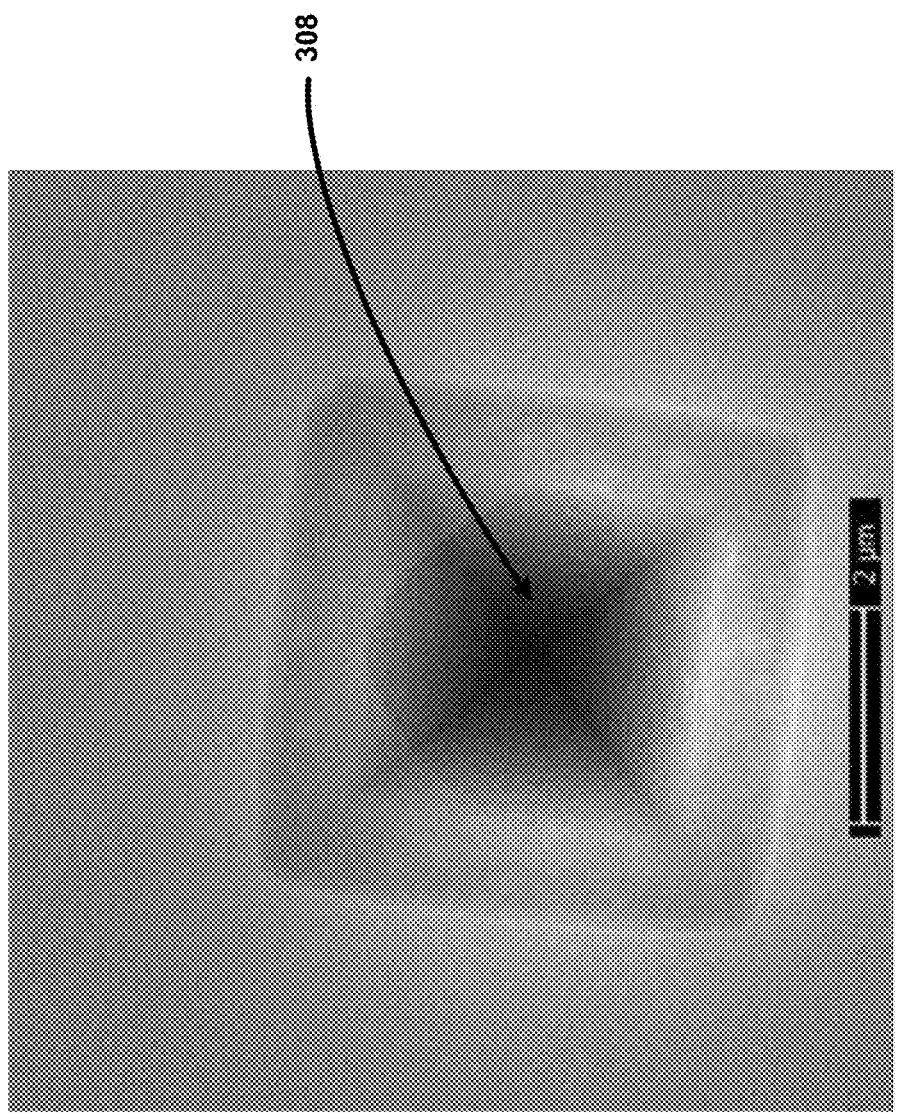
FIG. 6 illustrates a nanopore formed in accordance with various exemplary embodiments of the disclosure.

The fabrication process illustrated in FIG. 3 is based on the chemical-stop etching. Such techniques generally yield either pyramidal holes or circular-conical holes; an exemplary pyramidal hole is illustrated in FIG. 6, which show an etched feature 308 (or portion thereof) though a substrate. The principle idea is to stop base-etching of the silicon nanopore at the nanopore-location, once nanopore etch-through has occurred, by way of using an acidic buffer solution (or weak acidic solutions) at the other end of the silicon film. When base-etchant (e.g., tetramethylammonium hydroxide (TMAH) or KOH) etches through the thin silicon membrane, forming a sub-10 nm nanopore, $OH^-$ radicals from base etchant instantly meet $H^+$ radicals from acidic buffer solutions on other side, forming water molecules and salt. Consumption of $OH^-$ radicals at the nanopore interface leads to instantaneous stopping of any further etching of nanopore. Using a feedback electrical sense circuit 312, to measure conduction across the nanopore due to base-acid neutralization, any further etching of nanopore is stopped. This two-step etch-stop process: chemical etch-stop combined with electrical feedback etch-stop is expected to yield much higher control of nanopore fabrication. This chemical-stop etch process can be used for fast, precise fabrication of controlled nanopores in many different kinds of substrate materials. Neutralization reaction at the nanopore is an exothermic process. Hence weak acidic buffer solutions (~pH from 2 to 6) are used, where acidic buffer pH value, its buffer capacity and TMAH concentration may be process variables.

Capacitance and Resistance Based Measurements for Residual Silicon Thickness

Using CV measurements in addition to resistance/conductance measurement, can be used to monitor the residual thickness of silicon film while it is being etched. With decreasing silicon thickness, as it is etched, the capacitance of silicon at the nanopore location is expected to vary (increase), which can be measured and correlated.

Another Method for Nanopore Fabrication:

Backside of the substrate can be coated with a metal or semiconducting conducting layer thin film, and the conductivity (or capacitance) between the solution on etching side and this back conducting film is monitored with time. When a nanopore is formed on the substrate, the etching fluid comes into contact with back metal or conductive film, which causes a large change in conductivity or capacitance or impedance. By measuring conductivity (or capacitance or impedance) at high frequency voltage bias, and stopping the etch reaction when the conductivity changes, very accurate nanopores (e.g., having defined features such an a size of an opening) can be formed.

Alternate Methods for Nanopore Fabrication:

Alternatively, nanopores can be fabricated using methods and instruments such as electron beam milling, FIB (focused ion beam), ion beam sculpting, or other suitable technique.

Additionally, a nanopore (or a micro pore) once formed might be narrowed or shrunk down (i.e., its diameter at the opening reduced) further by growing an additional layer such as thermal silicon dioxide. Or, a nanopore can be shrunk/narrowed using electron beam techniques or ion beam/laser based or other local thermal heating based methods.

Methods of making nanopores, both solid state and biological nanopores, are listed in the following publications, which are included herein by their reference in their entirety, to the extent their contents do not conflict with the present disclosure.

*Nanopore sensors for nucleic acid analysis*, Bala Murali Venkatesan & Rashid Bashir *Nature Nanotechnology*, 6, 615-624 (2011), doi: 10.1038/nnano.2011.129.

*Disease Detection and Management via Single Nanopore-Based Sensors* Reiner, Joseph E.; Balijepalli, Arvind; Robertson, Joseph W. F.; et al. *CHEMICAL REVIEWS* Volume: 112 Issue: 12 Pages: 6431-6451 DOI: 10.1021/cr300381m December 2012.

*Single molecule sensing with solid-state nanopores: novel materials, methods, and applications* Miles, B N (Miles, Benjamin N.) [1]; Ivanov, A P (Ivanov, Aleksandar P.) [1] et al. *CHEMICAL SOCIETY REVIEWS* Volume: 42 Issue: 1 Pages: 15-28 DOI: 10.1039/c2cs35286a 2013.

*Electron-beam-induced deformations of SiO2 nanostructures* Storm, A J (Storm, A J); Chen, J H (Chen, J H); Ling, X S (Ling, X S); Zandbergen, H W (Zandbergen, H W); Dekker, C (Dekker, C) *JOURNAL OF APPLIED PHYSICS* Volume: 98 Issue: DOI: 10.1063/1.1947391 Jul. 1, 2005.

Self-Aligned Nanopore Fabrication

Figure 4:
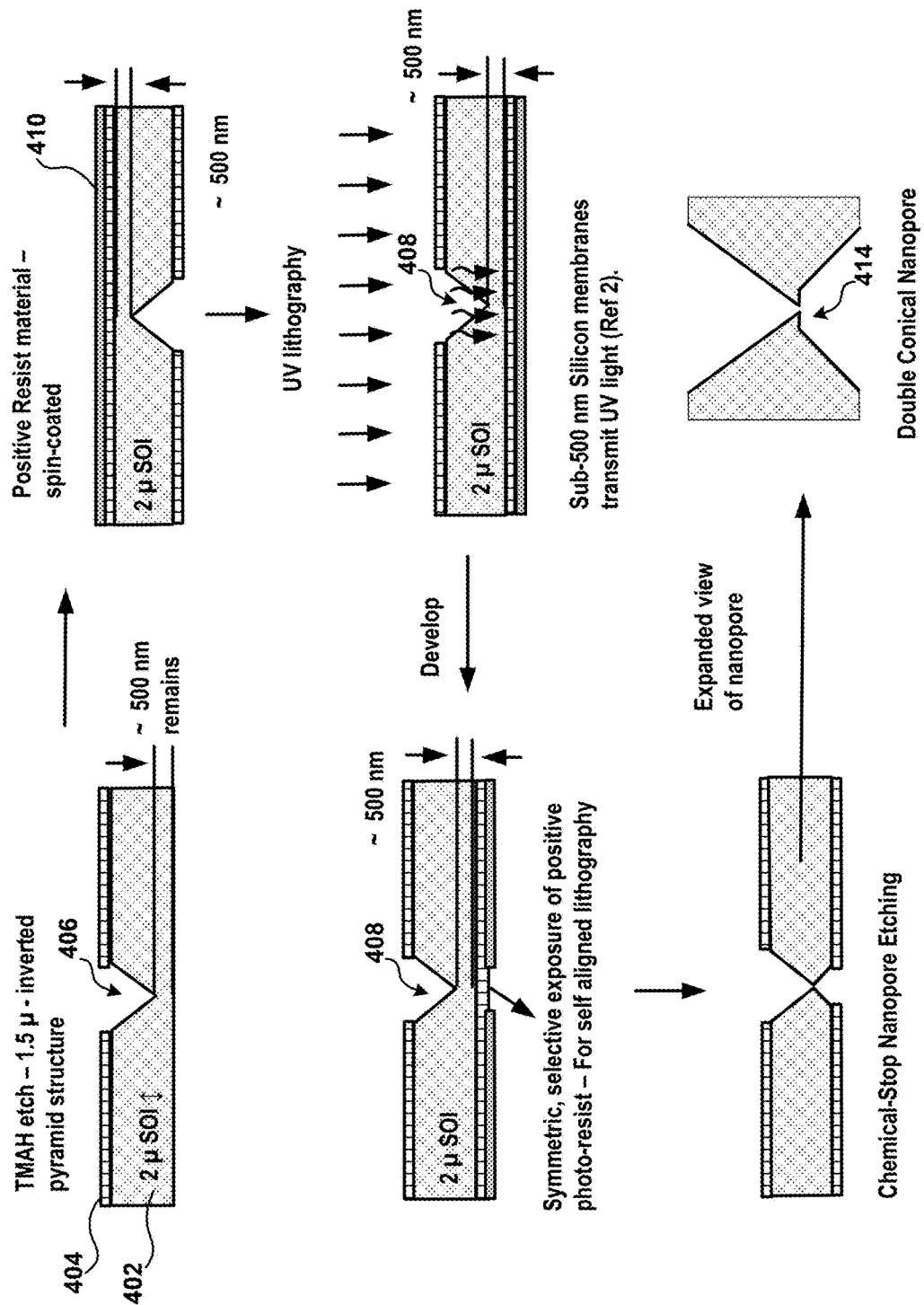
FIG. 4 illustrates steps of forming a field effect transistor device in accordance with exemplary embodiments of the disclosure.

FIG. 4 illustrates one exemplary structure for nanopore device fabrication, which includes a "self-aligned mask formation" on the bottom-side for single or double nanopore (e.g., conical, pyramidal, or the like) formation. The double etched-feature structure serves two purposes: (1) towards formation of nanopore point location for high sensitive FET signal transduction and (2) self-aligned mask on the double structure is desired for fabrication of self-aligned implantation-barrier masks on both sides for oxygen ion implantation, for buried oxide formation. Fabrication of a self-aligned mask is done by, for example, taking advantage of UV transmittance through, e.g., sub-500 nm silicon membranes. Other than trace UV transmittance, infrared-lithography, x-ray lithography and e-beam patterning techniques may also be used. Alternately, a sub-100 nm nanopore (or a sub-micron pore) may be formed first, and a self-aligned mask may be formed by using the UV light (or e-beam or X-ray light) transmitted out of the nanopore to pattern resist coated on the other side. The nanopore so formed may be shrunk/narrowed by, for example, depositing a thin film, growing a thermal film or using e-beam/thermal induced deformations.

To form the double nanopore, an etch feature (e.g., conical, inverted pyramid, or the like) 408 (~1.5 µm) is etched into patterned SOI substrate 402 (~2 µm) using a mask (e.g., SiN) 404, having an opening 406. Following this, positive UV photo-resist 410 is spun on the back side of the wafer (on top of nitride thin film). Due to UV transmittance through thin silicon films or using UV transmittance through nanopore, back side resist is exposed by UV incidence on front side, to yield self-aligned resist window 412, symmetric to top etch area 408. Alternately self-aligned mask is produced by using nanoparticles or beads at in the etched areas as mask. Or patterning masks using focused ion beam or scattering deposition or e-beam deposition or other techniques may be used. The self-aligned mask formed on both sides is used as mask for SIMOX oxygen implantation. After buried oxide formation by implantation, using nitride film 404 as base-etch mask, as shown in FIG. 4, chemical-stop nanopore fabrication technique is used to realize self-aligned single or double nanopore 414.

Double-Feature Nanopore on Silicon on Insulator (SOI, 1 to 1000 µm Thin Film)

When SOI substrates are used as base material for device fabrication, the back of the substrate silicon may be etched away along with the buried oxide (BOX) layer, and the device nanopore is realized on the SOI thin film, which is approximately 1 to 2000 micron thick. In one exemplary case, the thickness of initial SOI film is in between 2 micron to 1000 micron.

Self-Aligned Oxygen Implantation Mask Fabrication

Alternately, self-aligned oxygen implantation mask can be fabricated by first depositing an oxygen implantation mask layer such as nitride, chrome thin film, followed by photo-resist spinning. Photo resist, due to being viscous liquid, will fill the feature (e.g., conical or inverted pyramidal structures). After soft-baking the photo resist the wafer is treated to oxygen plasma where most of the photo-resist on the top is completely etched away, only photo resist in the recessed areas survives. The Chrome thin film is etched with patterned resist as a mask. The chrome layer is then used as etch-mask for nitride-etch in a reactive ion etch process.

Oxygen Implantation and Annealing for Buried Oxide

Figure 5:
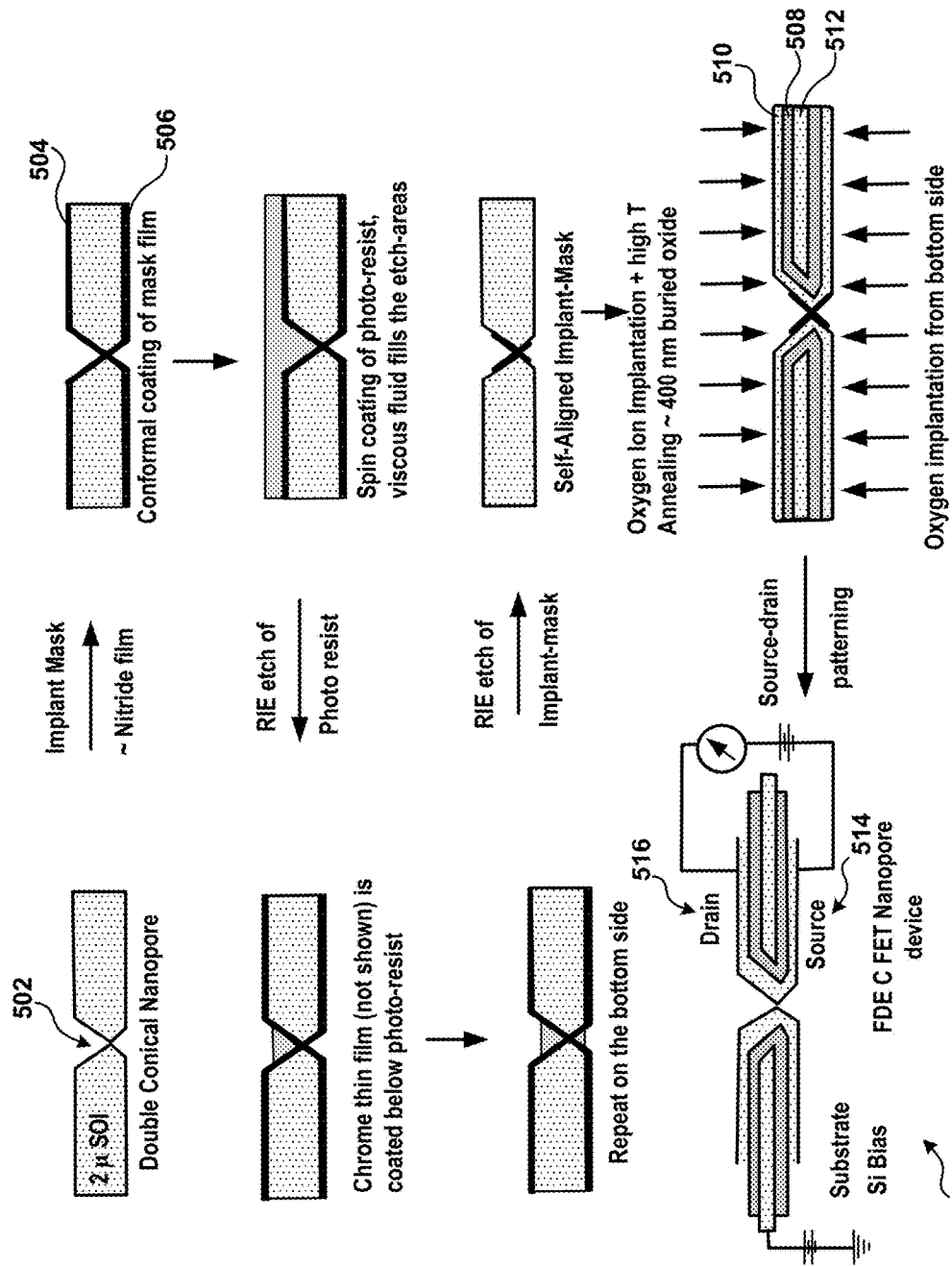
FIG. 5 illustrates steps of forming a field effect transistor device in accordance with exemplary embodiments of the disclosure.
Figure 10:
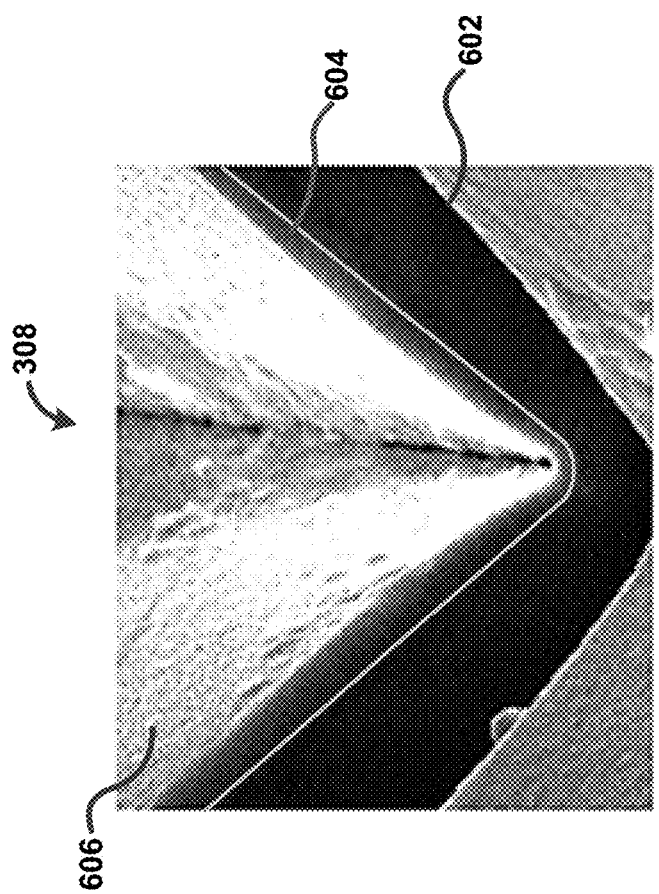
FIG. 10 illustrates another exemplary nanopore in accordance with exemplary embodiments of the disclosure.

With reference to FIG. 5, once a single or double structure 502 is formed, nitride masks 504, 506 for oxygen implantation are formed. Oxygen implantation layer 508 will isolate the silicon channel 510 from the silicon buried gate 512 that is used to bias the channel into inversion, accumulation or depletion, desired for device exponential coupling. Following oxygen implantation and the subsequent annealing steps, to yield buried oxide double layer, the wafer is ready for photo patterning. FIG. 10 illustrates an etch feature or structure 308 formed though a substrate including a buried or substrate silicon layer 602, buried oxide layer 604, and a top semiconductor layer 606. according to this technique.

The following publication discussing SIMOX implantation and buried oxide formation on silicon wafers and etched silicon wafers is included here in its entirety by reference.

*Fabrication of* [110]-aligned Si quantum wires embedded in SiO2 by low-energy oxygen implantation Yukari Ishikawa a, N. Shibata S. Fukatsu

*Nuclear Instruments and Methods in Physics Research* B 147 (1999) 304±309

Photo Patterning and Defining of Device

Once the various pores and layers are formed, photo patterning is used to isolate and/or provide access to each of the three layers—buried silicon gate 512 that is sandwiched between buried oxide layer 508; buried oxide layer 508 acting a gate oxide for the FET device; the silicon channel is then patterned using conventional lithography (on both sides) to open windows in nitride mask layers, followed by n+ doping to form source region 514 and drain region 516 on either side of structure 518. Metal contacts may then be formed to the source 514, drain 516 and the buried gate regions 508—to realize a functioning MOSFET device.

ALD Conformal Dielectric Coating on FDEC Nanopore Active Device Surface

To achieve high control of surface states at the Top silicon-oxide interface, the native oxide is replaced by select dielectric materials that are coated using atomic layer deposition in conformal fashion.

Characterization and Testing, Process Improvements for 1 Mhz Operational Devices Standard n-MOS characterization and processing optimization steps are used to improve device performance characteristics.

Other Methods of Nanopore Fabrication:

Formation of top semiconductor film of device using MBE, CVD or other techniques can be done as follows:

Step 1: Fabricate a nanopore in silicon or any semiconductor material or any conductor material.

Step 2: Deposit or grow or coat the above nanopore device with oxide or nitride or any other CMOS related dielectric material as defined in previous section.

Step 3: Deposit or grow or coat another crystalline or poly-crystalline or amorphous semiconductor material film or metal material film or insulator material film on top of the above structure.

Step 4: Use this structure as a FET structure, by forming source drain regions if needed, which can be used to sense the translocation of biomolecules (such as proteins or DNA) passing through the nanopore as described in the rest of the application or other materials as noted herein.

The methods described herein may also include forming at least one lipid bilayer overlaying a nanopore and/or adding a biological and/or chemical substance to the structure to form a biological and/or chemical nanopore.

Method of Using the Device

The devices described herein can be used to detect and characterize a variety of materials, including organic molecules, ionic species, nanoparticles, molecular species, materials selected from the group consisting of a DNA molecule, a protein molecule, a peptide molecule, a polypeptide molecule, an RNA molecule, a synthetic oligonucleotide molecule, and a synthetic peptide or polypeptide molecule, or a combination of these materials, and any of these materials modified with at least one tag selected from the group consisting of metal species, metal-organic species, chemical modifiers, biomolecular tags, complementary hybridizing chain molecules, peptides, polypeptides, oligonucleotides, zinc fingers, nano particles, quantum dots, organic dyes, beads, nanowires, and nanotubes.

Figure 8:
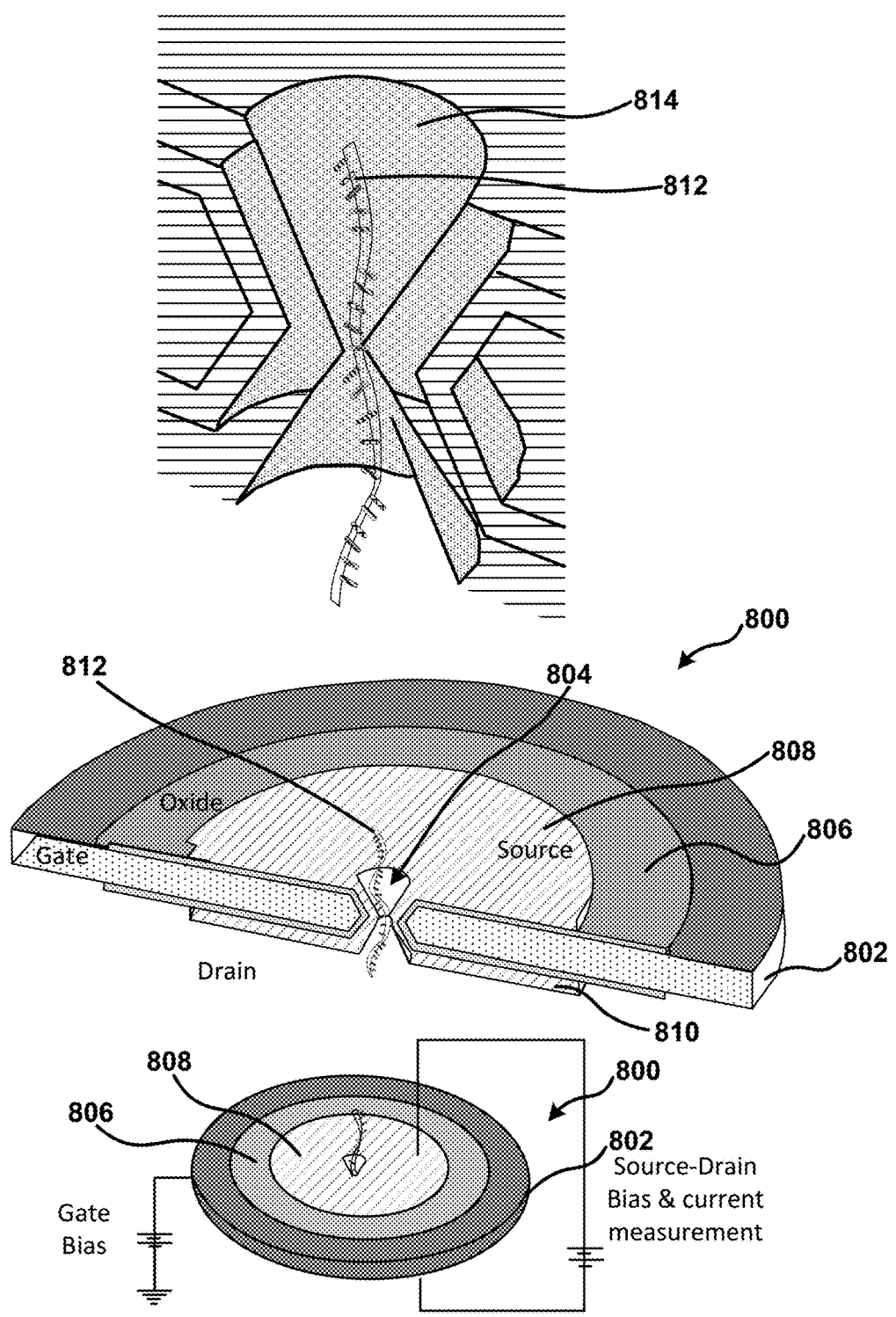
FIG. 8 illustrates a method of detecting material in accordance with additional exemplary embodiments of the disclosure.

FIG. 8 illustrates a device 800, including a substrate 802, an etch region 804, an insulating region 806, a source region 808 formed overlying insulating region 806 and overlying a first surface of the substrate 802, and a drain region 810 formed overlying insulating region 806 and overlying a first surface of the substrate. During operation of device 800, material 812 to be detected and/or characterized passes through a nanopore 814 of device 800.

Methods for Sequencing:

(a) Sequencing of Unmodified ssDNA:

As discussed in the previous sections, devices as described herein can be operated as sensor in different modes of operations, viz potential coupled mode and charged coupled mode. Base charge induced potentials on nanopore capacitor electrodes on the order of a milli volt have been reported in literature, varying between bases in magnitude and spatial distribution, calculated in response to external applied fields in a nanopore capacitor. Potential variation on the order of few hundred micro volts to milli volts should be detectable by operation of a device as described herein in potential coupled mode (device has very less defect states). A DNA nucleotide translocating at high speeds of microseconds per base through a nanopore constriction of few nm in diameters, sees an AC signal at 100 K to 1M Hz frequencies and an amplitude of few hundred micro volts. Such potential variation will be amplified at an edge of the nanopore, and further by the device coupling with the inversion channel. Device coupling with inversion or accumulation channel may be exponential in fully depleted films. An FET device operating at or above 10 MHz frequencies with internal amplification factor (combined amplification due to nanopore-curvature field and device coupling) is expected to be able to detect an unmodified DNA nucleotide passing at mega base per second speeds.

The above mentioned potential variation during translocation through a nanopore device is associated with charge variations, more specifically dipole variations between individual bases. Such charge, dipole variations can be read by a device in accordance with the present disclosure in charge coupled mode. We have demonstrated using a planar device charge, dipole coupling sensitivity up to few parts per trillion in gaseous phase detection of amine ligation. Using a device in accordance with the present disclosure, one expects charge coupling to be amplified further, with higher selectivity of base readout. But the read out speed in charge coupling mode is limited by interface trap state coupling speed which is in milli second time scales. Hence device charge coupling is slower than device potential coupling by orders of magnitude.

The present methods may be used on modified DNA nucleotides and on unmodified DNA.

(b) Sequencing by Hybridization:

In accordance with various embodiments of the disclosure, a method uses ssDNA hybridized with 7-mer probe strands. As one example, the 7-mer probe strand will consist of a combination of 4-mer combinatorial base sequences and a 3-mer universal base common to all combinations. Using this approach, translocation of a lengthy DNA strand with discrete probe hybridized regions, passing through the nanopore at mega base per second speeds, is detectable with much higher sensitivity compared to a unmodified DNA strand. This would then need a total of $4^4$ (256) separate probe hybridized translocation experiments for sequencing of a full genome.

(c) Sequencing of Chemically Modified ssDNA:

Another method of investigation for optimized potential and charge transduction using a device in accordance with the present disclosure is chemical modification of DNA strands in base selective fashion. Chemical modifications can use charged species or bulk moieties such as base selective DNA, organic molecule, peptide, protein molecules or metal or metal-organic moieties. Such base specific modification on single stranded DNA enables sequencing via translocation through use of devices of the present disclosure. Examples of chemical modification of bases are: Translocation of RecA-coated double-stranded DNA through solid-state nanopores; chemical modification of thymine-osmium oxidation of thymine; detection of methylated cytosine as one approach to cytosine sequencing; or cytosine can be chemically labeled and sequencing by sulphonation followed by deamination; chemical modification of guanine-methylene-blue sensitized photo-oxidation of guanine can be used to selective sequence guanine occurrence in the DNA strand.

High Fidelity DNA sequencing using RCDAs:

Devices in accordance with exemplary embodiments of the disclosure can be designed, fabricated and operated as n-channel devices or as a p-channel devices with a hole inversion layer formed at, for example, the oxide-silicon channel interface. Since fabrication of these devices may be based on CMOS VLSI technology, it is possible to fabricate both n-channel and p-channel devices side-by-side with a few hundred micron spacing between them.

The purpose of having both n-channel and p-channel device nanopores is that their respective responses to potential and charge variations at the point nanopore location will be in opposite directions. A small increase in potential applied to sensitive surface of an n-channel device sensor produces an increase in inversion current (decrease in threshold voltage). Similar increase in potential produces a decrease in p-channel FDEC FET sensor. A time varying potential due to high speed molecular transport events through the nanopore, or equivalently, a small (µV to nV)) oscillating A.C signal produces an amplified oscillating signal measured across source and drain, with opposite responses (i.e., 180 phase shifts) from n-channel and p-channel FDEC devices.

Furthermore amplified sensing along similar lines is expected to happen when the semiconductor channel is biased into accumulation. An n-channel FET nanopore can be operated in FDEC inversion coupled mode or in amplified accumulation coupled mode, by simply biasing the gate at either ends of the Id-Vg curve. Alternately inversion or accumulation can be formed at the top surface of semiconductor film at the interface with solution, and the conductivity in this case can be modulated by changing the solution bias.

Each device may be fabricated in parallel with complementary p-channel and accumulation biased devices (along with few other possible variations). Each DNA segment may be sequenced simultaneously, with integrated microfluidics, using each of these different FET nanopore device transduction mechanisms. This will provide robust redundancy for attaining ultra-high fidelity DNA sequencing. Such arrays are termed redundant combinatorial detection arrays (RCDA).

Every formulation or combination of components described or exemplified can be used to practice the invention, unless otherwise stated. Specific names of compounds are intended to be exemplary, as it is known that one of ordinary skill in the art can name the same compounds differently. One will appreciate that methods, device elements, starting materials, and synthetic methods, other than those specifically exemplified can be employed in the practice of the invention without resort to undue experimentation. All art-known functional equivalents, of any such methods, device elements, starting materials, and synthetic methods, and are intended to be included in this invention. Whenever a range is given in the specification, for example, a temperature range, a time range, or a composition range, all intermediate ranges and sub ranges, as well as all individual values included in the ranges given are intended to be included in the disclosure. When a Markush group or other grouping is used herein, all individual members of the group and all combinations and subcombinations possible of the group are intended to be individually included in the disclosure.

The present invention has been described above with reference to a number of exemplary embodiments and examples. It should be appreciated that the particular embodiments shown and described herein are illustrative of the invention and its best mode and are not intended to limit in any way the scope of the invention. It will be recognized that changes and modifications may be made to the exemplary embodiments without departing from the scope of the present invention. These and other changes or modifications are intended to be included within the scope of the present invention.

What is claimed is:

1. A device comprising:
   a substrate comprising a first surface and an opposing second surface;
   an etch region within a portion of the substrate and extending from the first surface to the second surface;
   an insulating region proximate the etch region;
   a semiconductor layer overlying the insulating region;
   a source region formed using a first portion of the semiconductor layer, the source region overlying the insulating region and overlying the first surface;
   a drain region formed using a second portion of the semiconductor layer, the drain region overlying the insulating region and overlying the second surface; and
   a channel formed using a third portion of the semiconductor layer,
   wherein the channel spans between the source region and the drain region, and
   wherein the device comprises a nanopore through the etch region.

2. The device of claim 1, wherein the insulating region comprise a buried oxide.

3. The device of claim 1, further comprising a thin-film coating comprising one or more of dielectric, organic, inorganic, and biological material.

4. The device of claim 1, wherein the etch region comprises a conical or pyramidal or spherical shape.

5. The device of claim 1, wherein the device is operated at frequencies of: kilo hertz, megahertz, or giga hertz.

6. The device of claim 1, wherein the channel is formed as a bi-feature having an opening of less than 1000 nm.

7. The device of claim 1, wherein the channel is formed as a bi-feature having an opening of less than 10 nm.

8. A method of sensing an ion, atom, or molecule, the method comprising the steps of:
   providing a device according to claim 1;
   providing material to be sensed;
   passing the material through a nanopore of the device; and
   detecting a variation in an electrical property of the device as the material passes through the nanopore.

9. The method of claim 8, wherein the material to be sensed comprises one or more selected from the group consisting of a DNA molecule, a protein molecule, a peptide molecule, a polypeptide molecule, an RNA molecule, a synthetic oligo nucleotide molecule, and a synthetic peptide or polypeptide molecule.

10. The method of claim 8, wherein the material to be sensed is selected from the group consisting of organic molecule, a nanoparticle, an ionic species, and a molecular species.

11. The method of claim 8, wherein the material to be sensed is modified with at least one tag selected from the group consisting of metal species, metal-organic species, chemical modifiers, biomolecular tags, complementary hybridizing chain molecules, peptides, polypeptides, oligonucleotides, zinc fingers, nano particles, quantum dots, organic dyes, beads, nanowires, and nanotubes.

12. The method of claim 8, wherein the device operates in potential coupled mode.

13. The method of claim 8, wherein the device operates in charge coupled mode.

14. The method of claim 8, wherein the device operates in inversion mode.

15. The method of claim 8, wherein the device operates in a mode selected from one or more of: accumulation, depletion, partial depletion, full depletion, inversion and volume inversion mode.

16. A method of forming a sensor device, the method comprising the steps of:
   providing a substrate comprising a first surface and an opposing second surface;
   etching a portion of the substrate to form an etch region open to the first surface and the second surface to thereby form a nanopore;
   forming an insulating region proximate the etch region;

forming a thin film overlying the insulating region;
forming a source region overlying the first surface using the thin film; and
forming a drain region overlying the second surface using the thin film,
wherein a channel region spans between the source region and the drain region.

17. The method of claim 16, wherein the etching is along a crystalline plane of the substrate.

18. The method of claim 16, wherein the thin film is formed using a technique selected from the group consisting of: molecular beam epitaxy and chemical vapor deposition.

19. The method of claim 16, wherein the thin film comprises one or more of: crystalline material, poly-crystalline material, amorphous material, a metal, and an insulator.

* * * * *